(12) United States Patent
Sauvee et al.

(10) Patent No.: US 9,738,657 B2
(45) Date of Patent: Aug. 22, 2017

(54) HIGHLY EFFICIENT POLARIZING AGENTS FOR DYNAMIC NUCLEAR POLARIZATION

(71) Applicant: Bruker Biospin S.A.S., Wissembourg (FR)

(72) Inventors: Claire Sauvee, Bruz (FR); Gilles Casano, Port-de-Bouc (FR); Olivier Ouari, Marseilles (FR); Paul Tordo, Marseilles (FR); Fabien Aussenac, Haguenau (FR); Melanie Rosay, Bedford, MA (US)

( * ) Notice: Subject to any disclaimer, the term of this patent is extended or adjusted under 35 U.S.C. 154(b) by 111 days.

(21) Appl. No.: 14/783,134

(22) PCT Filed: Apr. 11, 2014

(86) PCT No.: PCT/EP2014/057439
§ 371 (c)(1),
(2) Date: Oct. 8, 2015

(87) PCT Pub. No.: WO2014/167121
PCT Pub. Date: Oct. 16, 2014

(65) Prior Publication Data
US 2016/0046643 A1 Feb. 18, 2016

(30) Foreign Application Priority Data
Apr. 11, 2013 (EP) ..................... 13290082

(51) Int. Cl.
*G01N 24/08* (2006.01)
*C07D 491/20* (2006.01)
*C07D 403/12* (2006.01)
*C07D 401/14* (2006.01)
*C07D 401/12* (2006.01)
*C07D 211/94* (2006.01)
*C07D 221/20* (2006.01)

(52) U.S. Cl.
CPC .......... *C07D 491/20* (2013.01); *C07D 211/94* (2013.01); *C07D 221/20* (2013.01); *C07D 401/12* (2013.01); *C07D 401/14* (2013.01); *C07D 403/12* (2013.01); *G01N 24/088* (2013.01)

(58) Field of Classification Search
CPC ...................................... G01N 24/08
USPC ........... 436/173; 544/230; 546/16, 187, 189, 546/190, 208; 424/9.33
See application file for complete search history.

(56) References Cited

U.S. PATENT DOCUMENTS

| | | | | | |
|---|---|---|---|---|---|
| 4,123,273 | A | * | 10/1978 | Ciurca, Jr. | G03C 5/44 430/336 |
| 4,124,564 | A | * | 11/1978 | Minagawa | C08K 5/109 252/403 |
| 6,084,015 | A | * | 7/2000 | Chino | B60C 1/00 524/189 |
| 6,117,276 | A | * | 9/2000 | Cunkle | C07B 63/04 203/57 |
| 6,268,441 | B1 | * | 7/2001 | Lynch | C08F 2/40 526/204 |
| 7,196,144 | B2 | * | 3/2007 | Ashiura | C08F 8/30 525/333.8 |
| 7,994,258 | B2 | * | 8/2011 | Koga | A61K 49/124 424/9.33 |
| 8,471,031 | B2 | * | 6/2013 | Schoning | C07D 211/94 544/198 |
| 2005/0107696 | A1 | | 5/2005 | Griffin et al. | |
| 2005/0222343 | A1 | * | 10/2005 | Ashiura | C08F 8/30 525/333.7 |
| 2009/0302842 | A1 | * | 12/2009 | Griffin | C07D 401/12 324/309 |
| 2010/0249386 | A1 | * | 9/2010 | Ouari | C07D 471/18 530/409 |
| 2010/0249401 | A1 | * | 9/2010 | Schoning | C07D 211/94 544/2 |
| 2016/0052934 | A1 | * | 2/2016 | Ouari | C07D 491/22 324/309 |

FOREIGN PATENT DOCUMENTS

EP 0729947 A1 9/1996
WO 2008048714 A2 4/2008

OTHER PUBLICATIONS

Miura, Y. et al, Macromolecules 2001, 34, 447-455.*
Kiesewetter, M. K. et al, Journal of the American Chemical Society 2012, 134, 4537-4540.*
Morozov, D. A. et al, Journal of Organic Chemistry 2012, 77, 10688-10698.*
Ma, Z. et al, Journal of Organic Chemistry 1993, 58, 4837-4843.*
Okazaki, S. et al, Free Radical Research 2007, 41, 1069-1077.*
Kathirvelu, V. et al, Chemical Communications 2009, 454-456.*
Kinoshita, Y. et al, Free Radical Research 2009, 43, 565-571.*
Rajca, A. et al, Chemistry—A European Journal 2010, 16, 5778-5782.*
Yamasaki, T. et al, Journal of Organic Chemistry 2011, 76, 435-440.*
Sauvée et al., Highly Efficient, Water-Soluble Polarizing Agents for Dynamic Nuclear Polarization at High Frequency, Angewandte Communications, 52, 10858-10861, Ed. 2013.

(Continued)

*Primary Examiner* — Arlen Soderquist
(74) *Attorney, Agent, or Firm* — Benoît & Côté Inc.

(57) ABSTRACT

The invention relates to compounds of general formula (I) wherein X is C=O or $SO_2$, M is $NR^2$ or O, and $Q^1$ and $Q^2$ are nitroxide-containing radicals, and their use as a Dynamic Nuclear Polarization (DNP) agent for polarizing an NMR-active spin of a nucleus of an analyte in Nuclear Magnetic Resonance (NMR) spectroscopy.

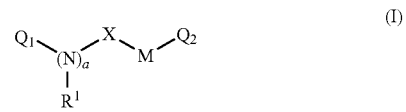

21 Claims, 1 Drawing Sheet

(56) References Cited

OTHER PUBLICATIONS

Niaik et al., Synthesis and Applications of Optically Active Nitroxides, Tetrahedron report No. 438, 667-696, 1998.

Schattling et al., Multi-responsive copolymers: using thermo-, light- and redox stimuli as three independent inputs bwards polymeric information processing, Chem. Commun., 47, 8859-8861, 2011.

Keana, Newer Aspects of the Synthesis and Chemistry of Nitroxide Spin Labels, Chemical Reviews, vol. 78, No. 1, 37-64, 1978.

Hu et al., High-frequency dynamic nuclear polarization using biradicals: A multifrequency EPR lineshape analysis, The Journal of Chemical Physics, 128, 052302, 2008.

Neumayer et al., Approaches to Alkaline Earth Metal-Organic Chemical Vapor Deposition Precursors. Synthesis and Characterization of Barium Fluoro-β-ketoiminate Complexes Having Appended Polyether "Lariats", Inorganic Chemistry, vol. 37, No. 21, 5625-5633, 1998.

Song et al., TOTALPOL: A Biradical Polarization Agent for Dynamic Nuclear Polarization Experiments in Aqueous Media, J. Am. Chem., Soc., vol. 128, No. 35, 11385-11390, 2006.

Kudo et al., Identification of Absolute Helical Structures of Aromatic Multilayered Oligo (m-phenylurea)s in Solution, J. Org. Chem., vol. 74, No. 21, 8154-8163, 2009.

Akai et al., Synthesis of Long-Chain [18F] Deoxyfluoropoly (ethylene glycol) Methyl Ethers and Their Noninvasive Pharmacokinetic Analysis by Positron Emission Tomography, Molecular Phamaceutics, vol. 8, No. 1, 302-308, 2010.

Abdel-Magid et al., Reductive Amination of Aldehydes and Ketones with Weakly Basic Anilines Using Sodium Triacetoxyborohydride, R.W. Johnson Pharmaceutical Research Institute, 537-539, Sep. 1990.

Rozantsev et al., Synthesis and Reactions of Stable Nitroxyl Radicals, II. Reactions, Institute of Chemical Physics, Academy of Sciences of the USSR, Moscow, 401-414, Aug. 1971.

Rozantsev et al., Synthesis and Reactions of Stable Nitroxyl Radicals, I. Synthesis, Institute of Chemical Physics, Academy of Sciences of the USSR, Moscow, 190-202, Apr. 1971.

Volodarsky et al., Synthesis and Reactions of a-Hydroxylamino-oximes, Institute of Organic Chemistry, Siberian Division of the Academy of Sciences of the U.S.S.R., 704-715, Sep. 1986.

Sakai et al., Effective 2,6-substitution of piperidine nitroxyl radical by carbonyl compound, Tetrahedron, 66, 2311-2315, 2010.

Ysacco, C. et al., Properties of dinitroxides for use in dynamic nuclear polarization (DNP), Physical Chemistry Chemical Physics, vol. 12, No. 22, 5841-5845, May 10, 2010.

Oulog, L. et al., Magnetic interaction in an amide containing two separate nitroxyl radicals, Advanced Materials, vol. 4, No. 5, 349-351, 1992.

Yoh Matsuki et al., Dynamic nuclear polarization with a rigid biradical, Angewandte Chemie, International Edition, vol. 48, No. 27, 4996-5000, Jun. 22, 2009.

\* cited by examiner

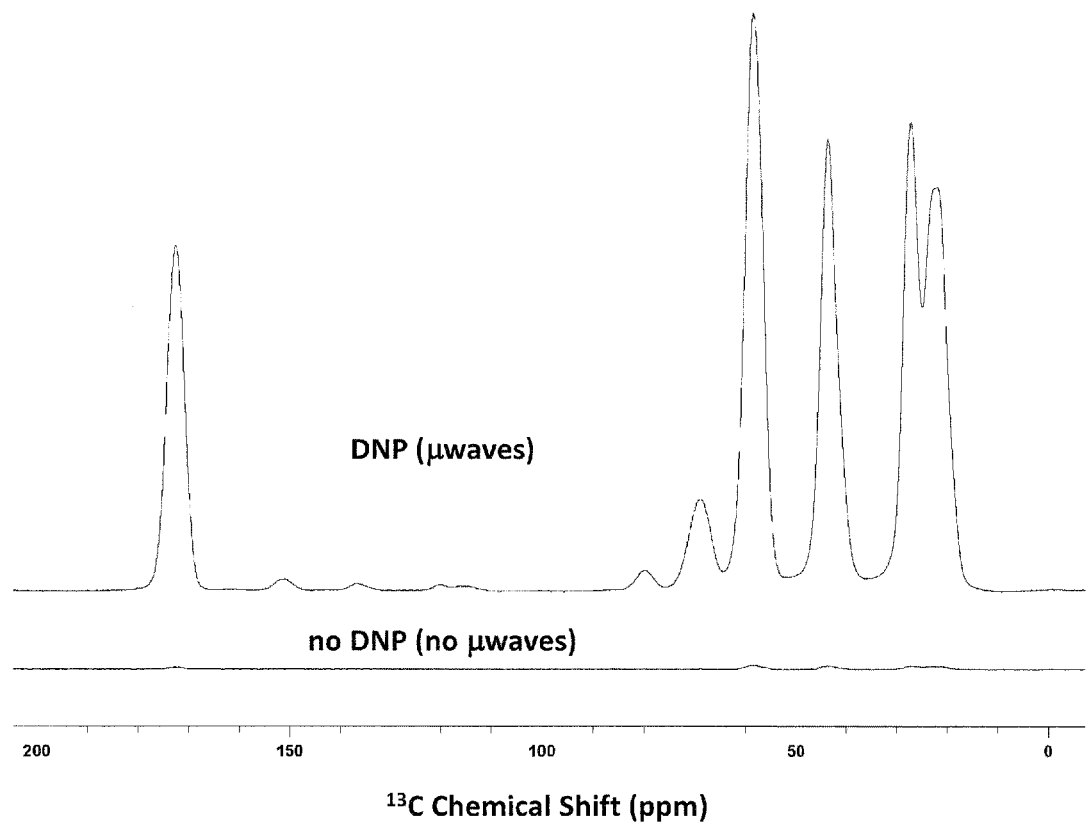

HIGHLY EFFICIENT POLARIZING AGENTS FOR DYNAMIC NUCLEAR POLARIZATION

FIELD OF THE INVENTION

The present invention relates to novel bis-nitroxide compounds and their use as Dynamic Nuclear Polarization (DNP) agents in Nuclear Magnetic Resonance (NMR) spectroscopy.

BACKGROUND OF THE INVENTION

In the method of Dynamic Nuclear Polarization (DNP) the polarization of unpaired electron spins which in thermal equilibrium is much larger than that of nuclei having spin half or uneven multiples thereof is transferred by high frequency microwave irradiation to nuclear spins so as to enhance their NMR sensitivity. Only electron paramagnetic resonance (EPR)-active spins (unpaired electrons, also referred to as paramagnetic centers or radicals) are eligible for this polarization process. The electron spin system in DNP may be provided by an endogenous or exogenous paramagnetic polarizing agent. Most often in this technique a paramagnetic agent is added to the sample of interest.

Initially, compounds comprising one nitroxide radical or other g≈2 paramagnetic center were utilized as DNP agents for NMR applications. To improve DNP efficiency, the research groups of Robert Griffin and Timothy Swager from MIT introduced biradical polarizing agents consisting of two paramagnetic centers tethered together. For the last 7 years, the TOTAPOL biradical (U.S. Pat. No. 7,351,402 B2, WO 2008/048714, C. Song et al., J. Am. Chem. Soc., 2006, 128(35), 11385) has been the most widely used polarizing agent for biological applications due to its high solubility in aqueous solutions, high stability, and good DNP efficiency.

In 2008, the group of Robert Griffin and Timothy Swager disclosed 4,4-ureylene-di-(2,2,6,6-tetramethylpiperidinyloxyl) ("bis-TEMPO-urea" or "bTurea") for use as a DNP agent (K. H. HU, C. Song, H. Yu, T. Swager, and R. Griffin J. Chem. Phys. 128, 052302 (2008)).

The present invention seeks to provide further dinitroxide compounds with improved DNP efficiency and/or solubility properties since the efficiency of polarizing agents for specific applications depend on a number of factors including the polarizing agent, analyte, solvent, and experimental conditions.

SUMMARY OF THE INVENTION

In a first aspect, the present invention relates to a compound of general formula (I)

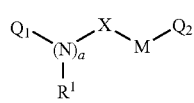
(I)

wherein:
M is $NR^2$ or O
X is CO or $SO_2$
a is 1 or 0;
$R^1$ is H; $(CH_2)_o$-E, wherein o is an integer of from 1 to 10 and E is COOH, OH, $NH_2$,
$N_3$, C≡CH, $P(O)(OH)_2$, $P(O)(OR^{13})_2$, $P(O)(OR^{13})(R^{13})$, $P(O)R^{13}_2$ or $SSO_2Me$; $(CH_2-CH_2-O)_m-CH_3$ or $(CH_2-CH_2-O)_m-H$, wherein m is an integer of from 1 to 500; or

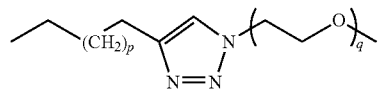

wherein p is an integer of from 0 to 7 and q is an integer of from 1 to 500;
$R^2$ is independently as defined for $R^1$;
or
if X is CO, a is 1 and M is $NR^2$, $R^1$ and $R^2$ form together with the group X and the atoms to which they are bound a 5- or 6-membered heterocyclic ring which may be substituted;
and
$Q_1$ and $Q_2$ are independently of each other a cyclic or acyclic nitroxide of formula:

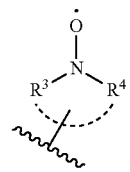

wherein
$R^3$ and $R^4$ are, independently, a substituted or unsubstituted linear, branched or cyclic $C_{1-6}$ aliphatic group; a substituted or unsubstituted linear, branched or cyclic group heteroaliphatic group comprising 5 C atoms and one heteroatom or heteroatomic group, respectively, selected from O, S, —$NR^{12}$—, $P(O)(OR^{13})$ and $P(O)(R^{13})$; substituted or unsubstituted aryl; substituted or unsubstituted heteroaryl, or substituted or unsubstituted 2,2,7,7-tetramethyl isoindolinoxyl; or
$R^3$ and $R^4$ are joined, as indicated by

to form together with the nitrogen atom to which they are bound a 5- to 8-membered heterocyclic ring and which may contain an additional heteroatom or heteroatomic group selected from $P(O)(OR^{13})$, $P(O)(R^{13})$, O, S, $N^+$—$O^-$, NH, $N(C_1-C_6$ alkyl) wherein the alkyl is straight, branched or cyclic, wherein the heterocyclic ring may contain one double bond and bears from one substituent to the maximum possible number of substituent on the carbon atoms;
and with the proviso that the two groups $R^3$ or $R^4$ together do not contain more than one hydrogen alpha to the (N—O.) group;
$R^{12}$ is hydrogen, hydroxyl; substituted or unsubstituted linear, branched or cyclic $C_{1-6}$ alkyl;
$C_{1-6}$ alkylcarbonyl; substituted or unsubstituted $C_{1-6}$ alkyl sulfonyl; substituted or unsubstituted $C_{1-6}$ alkyl sulfinyl; substituted or unsubstituted aryl sulfinyl; or substituted or unsubstituted aryl sulfonyl;
$R^{13}$ is linear or branched $C_{1-18}$ alkyl;

wherein the point of attachment of the nitrogen atom, the group X or the group M by a single bond, as indicated by

is to a primary or secondary non-olefinic or aromatic C atom of either $R_3$ or $R_4$, or to a C atom of the 5- to 8-membered heterocyclic ring formed by the joining of $R_3$ and $R_4$, except the compound 4,4-ureylene-di-(2,2,6,6-tetramethylpiperidinyloxyl

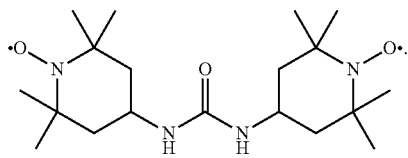

In a second aspect, the invention relates to the use of a compound according to the invention as a Dynamic Nuclear Polarization (DNP) agent for polarizing NMR-active nuclear spins of an analyte in Nuclear Magnetic Resonance (NMR) spectroscopy.

SHORT DESCRIPTION OF THE DRAWING

FIG. 1 shows an DNP experiment with Compound 58 ("AMUPOL") as a polarizing agent at 14.1 T, 600 MHz $^1$H frequency, 395 GHz microwave frequency.

DETAILED DESCRIPTION

At first definitions of specific functional groups, substituents and chemical terms relevant in the context of the present invention are described in more detail below.

For purposes of this invention, the chemical elements are identified in accordance with the Periodic Table of the Elements, CAS version, Handbook of Chemistry and Physics, 75th Ed., inside cover, and specific functional groups are generally defined as described therein. Additionally, general principles of organic chemistry, as well as specific functional moieties and reactivity, are described in Organic Chemistry, Thomas Sorrell, University Science Books, Sausalito, 1999; Smith and March March's Advanced Organic Chemistry, 5th Edition, John Wiley & Sons, Inc., New York, 2001; Larock, Comprehensive Organic Transformations, VCH Publishers, Inc., New York, 1989; Carruthers, Some Modern Methods of Organic Synthesis, 4$^{th}$ Edition, Cambridge University Press, Cambridge, 2004; the entire contents of each of which are incorporated herein by reference.

Certain parts or groups of the inventive compound as described herein may be substituted with any number of substituents or functional moieties. In general, the term "substituted" refers to the replacement of hydrogen radicals in a given structure with the radical of a specified substituent. When more than one position in any given structure may be substituted with more than one substituent selected from a specified group, the substituent may be either the same or different at every position. If a specific substituent meaning is indicated e.g. by a term "$R^1$, $R^2$ ... ", this specific substituent may also be a hydrogen atom.

The term "$C_1$-$C_6$ aliphatic group", as used herein, includes both saturated and unsaturated, nonaromatic, straight chain (i.e., unbranched), branched, acyclic and cyclic (i.e., carbocyclic) hydrocarbons having 1-6 C atoms, which are optionally substituted with one or more functional groups. The term "aliphatic" is herein includes $C_{1-6}$ alkyl, $C_{3-6}$ alkenyl, $C_{2-6}$ alkynyl, $C_{3-6}$ cycloalkyl, $C_{3-6}$ cycloalkenyl, and $C_{5-6}$ cycloalkynyl moieties. Thus, as used herein, the term "$C_{1-6}$ alkyl" includes straight, branched and cyclic $C_{1-6}$ alkyl groups. In an analogous manner, this is valid for the terms "$C_{2-6}$ alkenyl" and "$C_{2-6}$ alkynyl", Substituents in a substituted $C_{1-6}$ aliphatic group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen, hydroxyl, thiol, nitro, cyano; —$NR^c_2$, =$NR^c$, —COOH, COOR$^c$, —CONR$^c_2$, and SO$_2$NR$^c_2$, wherein R$^c$ is independently selected from the group consisting of H, $C_{1-4}$ hydroxyalkyl and $C_{1-4}$ alkyl; oxo, thiooxo, and azido groups. The number of substituents present in a substituted $C_1$-$C_8$ aliphatic group may be up to the number of the hydrogen atoms available for a substitution, but is preferably 1-2, more preferably 1.

The term "$C_{1-8}$ alkyl," as used herein, refers to saturated, straight- or branched-chain or cyclic hydrocarbon radicals derived from a hydrocarbon moiety containing from one to six carbon atoms by removal of a single hydrogen atom. Examples of $C_{1-6}$ alkyl radicals include methyl, ethyl, n-propyl, isopropyl, n-butyl, iso-butyl, sec-butyl, sec-pentyl, isopentyl, tert-butyl, n-pentyl, neopentyl, n-hexyl, sec-hexyl, cyclopropyl, cyclopropylmethyl, cyclopentyl and cyclohexyl. The term "$C_{1-4}$ alkyl" as used herein, refers to saturated, straight- or branched-chain hydrocarbon radicals derived from a hydrocarbon moiety containing from one to four carbon atoms by removal of a single hydrogen atom. Examples of $C_{1-4}$alkyl radicals include methyl, ethyl, n-propyl, isopropyl, n-butyl, iso-butyl and sec-butyl. The term "$C_{3-7}$ cycloalkyl" refers to cyclic hydrocarbon radicals derived from a hydrocarbon moiety containing from one to seven carbon atoms by removal of a single hydrogen atom. Examples of $C_{3-7}$ cycloalkyl include cyclopropyl, cyclopropylmethyl, cyclobutyl, cyclobutylmethyl, cyclopentyl, cyclopentylmethyl, cyclohexyl and cyclohexylmethyl. The term "$C_{1-18}$ alkyl" refers to straight- or branched-chain hydrocarbon radicals derived from a hydrocarbon moiety containing from one to eighteen carbon atoms by removal of a single hydrogen atom The above-mentioned alkyl or cycloalkyl groups which may bear one or more substitutents. Substituents in a substituted $C_{1-6}$ alkyl group, $C_{1-4}$ alkyl group or $C_{3-7}$ cycloalkyl group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen, hydroxyl, thiol, nitro, cyano; —NR$^c_2$, =NR$^c$, —COOH, COOR$^c$, —CONR$^c_2$, and SO$_2$NR$^c_2$, wherein R$^c$ is independently selected from the group consisting of H, $C_{1-4}$ hydroxyalkyl and $C_{1-4}$ alkyl; oxo, thiooxo, and azido groups. The number of substituents present in a substituted $C_{1-6}$ alkyl group, $C_{1-4}$ alkyl group or $C_{3-7}$ cycloalkyl group may be up to the number of the hydrogen atoms available for a substitution, but is preferably 1-2, more preferably 1.

The term "$C_{2-6}$ alkenyl," as used herein, denotes a monovalent group derived from a straight- or branched-chain or cyclic hydrocarbon moiety having at least one carbon-carbon double bond by the removal of a single hydrogen atom. The $C_{2-6}$ alkenyl group contains 2-6 carbon atoms. $C_{2-6}$ alkenyl groups include, for example, ethenyl, propenyl, isopropenyl, 1- or 2-butenyl, 1-methyl-2-buten-1-yl and cyclopentenyl. $C_{2-4}$ alkenyl, as used herein, denotes a monovalent group derived from a straight- or branched-chain hydrocarbon moiety having at least one carbon-carbon double bond by the removal of a single hydrogen atom. The $C_{2-4}$ alkenyl group contains 2-4 carbon atoms. Examples are ethenyl, propenyl, isopropenyl and 1- or 2-butenyl.

The above-mentioned alkenyl groups may bear one or more substituents. Substituents in a substituted $C_{2-6}$ or $C_{2-4}$ alkenyl group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen, hydroxyl, thiol, nitro, cyano; —$NR^e_2$, =$NR^e$, —COOH, COOR$^e$, —CONR$^e_2$, and SO$_2$NR$^e_2$, wherein R$^e$ is independently selected from the group consisting of H, $C_{1-4}$ hydroxyalkyl and $C_{1-4}$ alkyl; oxo, thiooxo, and azido groups. The number of substituents present in a substituted $C_{1-6}$ alkenyl group may be up to the number of the hydrogen atoms available for a substitution, but is preferably 1-2, more preferably 1.

The term "$C_{2-6}$ alkynyl", as used herein, refers to a monovalent group derived from a straight- or branched-chain or cyclic hydrocarbon having at least one carbon-carbon triple bond by the removal of a single hydrogen atom. The $C_{2-6}$ alkynyl group employed in the invention contains 2-6 carbon atoms. Representative $C_{2-6}$ alkynyl groups include ethynyl, 2-propynyl (propargyl), 1-propynyl, and cyclohexynyl, "$C_{2-4}$ alkynyl" refers to a monovalent group derived from a straight- or branched-chain having at least one carbon-carbon triple bond by the removal of a single hydrogen atom. Representative $C_{2-4}$ alkynyl groups include ethynyl, 2-propynyl (propargyl), and 1-propynyl.

The above-mentioned alkynyl groups may bear one or more substituents. Substituents in a substituted $C_{2-6}$ or $C_{2-4}$ alkynyl group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen, hydroxyl, thiol, nitro, cyano; —$NR^e_2$, =$NR^e$, —COOH, COOR$^e_2$, and SO$_2$NR$^e_2$, wherein R$^e$ is independently selected from the group consisting of H, $C_{1-4}$ hydroxyalkyl and $C_{1-4}$ alkyl; oxo, thiooxo, and azido groups. The number of substituents present in a substituted $C_1$-$C_6$ alkynyl group may be up to the number of the hydrogen atoms available for a substitution, but is preferably 1-2, more preferably 1.

The term primary C atom denotes a C atom being bonded to one further C atom by a single bond and otherwise having hydrogen substituents only.

The term secondary non-olefinic C atom denotes a C atom being bonded to two further C atoms each by a single bond.

The term "$C_{1-6}$ heteroaliphatic group" as used herein, includes both saturated and unsaturated, nonaromatic, straight chain (i.e., unbranched), branched, acyclic, cyclic (i.e., heterocyclic) hydrocarbons, which are optionally substituted with one or more functional groups, and that contain one oxygen, sulfur, substituted nitrogen or substituted phosphorus atom in place of one carbon atom. A heteroaliphatic group according to the invention has 1-5 carbon atoms. The term "$C_{1-6}$ heteroaliphatic group" is includes heteroalkyl, heteroalkenyl, heteroalkynyl, and heterocyclyl moieties. Thus, as used herein, the term "heteroalkyl" includes straight, branched and cyclic alkyl groups, as defined herein, which are optionally substituted with one or more functional groups, and that contain one oxygen, sulfur, nitrogen or phosphorus atom in place of one carbon atom. An analogous convention applies to other generic terms such as "heteroalkenyl" and "heteroalkynyl". The substituent of the nitrogen atom is the substituent $R^{12}$, as defined below. Phosphorus is present as P(O)($C_{1-18}$ alkoxy) or P(O)($C_{1-16}$ alkyl). The term "substituted $C_{1-6}$ heteroaliphatic group" denotes that one or more carbon atoms may also bear a substituent.

Substituents on carbon atoms of the $C_{1-6}$ heteroaliphatic group include $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen, hydroxyl, thiol, nitro, cyano; —$NR^e_2$, =$NR^e$, —COOH, COOR$^e$, —CONR$^e_2$, and SO$_2$NR$^e_2$, wherein R$^e$ is independently selected from the group consisting of H, $C_{1-4}$ hydroxyalkyl and $C_{1-4}$ alkyl; oxo, thiooxo, and azido groups. The number of substituents present in a substituted $C_1$-$C_6$ heteroaliphatic group may be up to the number of the hydrogen atoms available for a substitution, but is preferably 1-2, more preferably 1.

One specific substituent of nitrogen atoms in the compounds of the invention is the substituent $R^{12}$ which may be hydrogen, hydroxyl; substituted or unsubstituted linear, branched or cyclic $C_{1-6}$ alkyl; $C_{1-6}$ alkylcarbonyl; substituted or unsubstituted $C_{1-6}$ alkyl sulfonyl; substituted or unsubstituted $C_{1-6}$ alkyl sulfinyl; substituted or unsubstituted aryl sulfinyl; or substituted or unsubstituted aryl sulfonyl; preferably $R^{12}$ is hydrogen, linear, branched or cyclic $C_{1-6}$ alkyl, which is unsubstituted or substituted with one hydroxyl.

The term "aryl," as used herein, refer to stable aromatic mono- or bicyclic ring system having 5-10 ring atoms, of which all the ring atoms are carbon, and which may be substituted or unsubstituted. Aryl includes phenyl, biphenyl and naphthyl, which may bear one or more substituents.

Aryl substituents include $C_{1-6}$ alkyl, $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen, hydroxyl, thiol, nitro, cyano; —$NR^e_2$, =$NR^e$, —COOH, COOR$^e$, —CONR$^e_2$, and SO$_2$NR$^e_2$, wherein R$^e$ is independently selected from the group consisting of H, $C_{1-4}$ hydroxyalkyl and $C_{1-4}$ alkyl; oxo, thiooxo, and azido groups.

2,2,7,7-Tetramethyl isoindolinoxyl substituents on the benzene ring are the same as the aryl substituents.

Preferably aryl is unsubstituted phenyl or phenyl substituted with one of the above substituents.

The term "heteroaryl," as used herein, refer to stable aromatic mono- or bicyclic ring system having 5-12 ring atoms, of which one ring atom is selected from S, O, and N; zero, one, or two ring atoms are additional heteroatoms independently selected from S, O, and N; and the remaining ring atoms are carbon, the radical being joined to the rest of the molecule via any of the ring atoms. Exemplary heteroaryls include pyrrolyl, pyrazolyl, imidazolyl, pyridinyl, pyrimidinyl, pyrazinyl, pyridazinyl, triazinyl, tetrazinyl, pyyrolizinyl, indolyl, quinolinyl, isoquinolinyl, benzoimidazolyl, indazolyl, quinolinyl, isoquinolinyl, quinolizinyl, cinnolinyl, quinazolynyl, phthalazinyl, naphthridinyl, quinoxalinyl, thiophenyl, thianaphthenyl, furanyl, benzofuranyl, benzothiazolyl, thiazolynyl, isothiazolyl, thiadiazolynyl, oxazolyl, isoxazolyl, oxadiaziolyl and oxadiaziolyl which may bear one or more substituents.

Heteroaryl substituents include $C_{1-6}$ alkyl, $C_{1-4}$ hydroxyalkyl, $C_{1-4}$ alkoxy, $C_{1-4}$ alkylthio; $C_{1-4}$ alkylcarbonyl; $C_{1-4}$ alkylsulfonyl; $C_{1-4}$ alkylsulfinyl, whose alkyl moieties may be partially or completely halogenated with independent halogen atoms; halogen, hydroxyl, thiol, nitro, cyano;

—NR$^c_2$, =NR$^c$, —COOH, COOR$^c$, —CONR$^c_2$, and SO$_2$NR$^c_2$, wherein R$^c$ is independently selected from the group consisting of H, C$_{1-4}$ hydroxyalkyl and C$_{1-4}$ alkyl; oxo, thiooxo, and azido groups.

Preferably heteroaryl is pyrrolyl, pyrazolyl, imidazolyl, pyridinyl, pyrimidinyl, pyrazinyl, pyridazinyl, furanyl and thiophenyl, each unsubstituted or substituted with one of the above substituents.

The term "heterocyclic ring", as used herein, refers to a non-aromatic, partially unsaturated or fully saturated, 5- to 8-membered ring. These heterocyclic rings include those having from one to three heteroatoms independently selected from oxygen, sulfur, phosphorus and nitrogen, in which the nitrogen, phosphorus and sulfur heteroatoms may optionally be oxidized and the nitrogen heteroatom may optionally be quaternized. In certain embodiments, the term heterocylic ring refers to a non-aromatic 5-, 6-, 7- or 8-membered ring wherein at least one ring atom is a heteroatom selected from O, S, P and N (wherein the nitrogen, phosphorus and sulfur heteroatoms may be optionally oxidized and the substitutent of the nitrogen atom is the substituent R$^{12}$, as defined above, and phosphorus is present as P(O)OR$^{13}$, P(O)(OR$^{13}$) or P(O)R$^{13}$, wherein R$^{13}$ is as defined above.), and the remaining ring atoms are carbon, the radical being joined to the rest of the molecule via any of the carbon ring atoms.

Substituents on carbon atoms of heterocyclic rings include C$_{1-6}$ alkyl, C$_{1-4}$ hydroxyalkyl, C$_{1-4}$ alkoxy, C$_{1-4}$ alkylthio; C$_{1-4}$ alkylcarbonyl; C$_{1-4}$ alkylsulfonyl; C$_{1-4}$ alkylsulfinyl, whose alkyl moieties may be partially or completely halogenated with independent halogen atoms; halogen, hydroxyl, thiol, nitro, cyano; —NR$^c_2$, =NR$^c$, —COOH, COOR$^c$, —CONR$^c_2$, and SO$_2$NR$^c_2$, wherein R$^c$ is independently selected from the group consisting of H, C$_{1-4}$ hydroxyalkyl and C$_{1-4}$ alkyl; oxo, thiooxo, and azido groups. Furthermore, any two geminal substituents of heterocyclic rings may be joined to form together with the secondary C atom to which they are bound a cyclopentane or cyclohexane ring which may be further substituted with one or more substituents as defined above in the context of the definition of alkyl groups, or a 5- or 6-membered heterocyclic ring comprising one atom or group selected from —O—, —S—, —N(R$^{12}$)—, —P(O)OH—, —P(O)(C$_{1-6}$ alkyl) and —P(O)(C$_{1-6}$ alkoxy) which may be further substituted on one or more carbon atoms with a substituent as defined above on this paragraph.

The term "hydroxy," or "hydroxyl," as used herein, refers to a group of the formula (—OH).

The term "C$_{1-4}$ alkoxy" refers to a group of the formula —OR, wherein R is C$_{1-4}$ alkyl. The term "C$_{1-18}$ alkoxy" refers to a group of the formula —OR, wherein R is linear or branched C$_{1-18}$ alkyl.

The term "C$_{1-4}$ hydroxyalkyl" refers to a C$_{1-4}$ alky group bearing one hydroxyl substituent in the place of any hydrogen atom.

The term "azido," as used herein, refers to a group of the formula (—N3).

The term "cyano," as used herein, refers to a group of the formula (—CN).

The term "direct bond" or "bond" refers to a single, double or triple bond between two groups. In certain embodiments a "direct bond" refers to a single bond between two groups.

The terms "halo" and "halogen" as used herein refer to an atom selected from fluorine (fluoro, —F), chlorine (chloro, —Cl), bromine (bromo, —Br), and iodine (iodo, —I).

The term "nitro," as used herein, refers to a group of the formula (—NO$_2$).

The term "nitroxide," as used herein, refers to a stable nitroxide group which may be cyclic or acyclic. In certain embodiments, a stable nitroxide refers to a chemically stable nitroxide which may be obtained in pure form, stored, and handled in the laboratory. In certain embodiments, a stable nitroxide refers to a cyclic or acyclic nitroxide which contains two groups which do not contain alpha hydrogens. Exemplary cyclic or acyclic nitroxides are provided in Keana, Chemical Reviews (1978) 78:37-64, the entirety of which is incorporated herein by reference.

The term "oxo," as used herein, refers to a group of the formula (=O).

The term "thiol," as used herein, refers to a group of the formula (—SH).

The term "thio," as used herein, refers to a group of the formula (—S—)

The term "thiooxo," as used herein, refers to a group of the formula (=S).

The term "C$_{1-4}$ alkyl sulfinyl" and "C$_{1-6}$ alkyl sulfinyl", as used herein, refers to a group of the formula C$_{1-4}$ alkyl-S(=O)— and C$_{1-6}$ alkyl-S(=O)—, respectively.

The term "aryl sulfinyl" as used herein, refers to a group of the formula aryl-S(=O)—

The term "C$_{1-4}$ alkyl sulfonyl" and "C$_{1-6}$ alkyl sulfonyl", as used herein, refers the group of the formula C$_{1-4}$ alkyl-S(=O)$_2$— and C$_{1-6}$ alkyl-S(=O)$_2$—, respectively.

The term "aryl sulfonyl" as used herein, refers to a group of the formula aryl-S(=O)$_2$—.

The nitroxide-containing groups $Q_1$ and $Q_2$ of the present invention are selected from the following groups, where the definitions are those given in the summary of the invention in conjunction with the above definitions:

aliphatic-NO-aliphatic;
aliphatic-NO-heteroaliphatic;
aliphatic-NO-aromatic;
aliphatic-NO-heteroaromatic;
heteroaliphatic-NO-heteroaliphatic;
heteroaliphatic-NO-aromatic;
heteroaliphatic-NO-heteroaromatic;
aromatic-NO-aromatic;  p aromatic-NO-heteroaroatic; and
heteroaromatic-NO-heteroaromatic;

wherein "aliphatic" is a substituted or unsubstituted linear, branched or cyclic C$_1$-C$_6$ aliphatic group; and "heteroaliphatic" is a substituted or unsubstituted linear, branched or cyclic group heteroaliphatic group comprising 5 C atoms and one heteroatom or hetero group, respectively, selected from O, S, N(R$^{12}$), P(R$^{12}$),) P(=O)OH and P(=O)O(C$_{1-6}$ alkyl); "aromatic" and "heteroaromatic" are substituted or unsubstituted "aryl" and "heteroaryl" respectively, as defined above; with the proviso that the two groups, which are selected from heteroaliphatic, aromatic or heteroaromatic group and are attached to the nitrogen atom of the (N—O.) group, together do not contain more than one hydrogen alpha to the (N—O.) group; and a nitroxide-containing 5- to 8-membered heterocyclic ring, which may contain an additional heteroatom or heteroatomic group selected from O, S, N$^+$—O$^-$, NH, N(C$_{1-6}$ alkyl) wherein the alkyl is straight, branched or cyclic, and may contain one double bond and is substituted at least at all positions alpha to the (N—O.) group, the substituents being selected from those mentioned above in the context of the definition of "heterocyclic group";

The synthesis of those groups is known to the person skilled in the art; see, for example (a) E. G. Rozantsev and V. D. Sholle, *Synthesis*, 190-202 (1971). (b) E. G. Rozantsev and V. D. Sholle, *Synthesis*, 410-414 (1971). (c) E. G. Rozantsev and V. D. Sholle, *Synthesis*, 895-916 (1984). (d) J. F. W. Keana, *Chem. Rev.* 1978, 78, 37-64 (e) A. R. Forrester, J. M. Hay and R. H. Thomson, *Organic Chemistry of Stable Free Radicals*, Academic Press, New York, N.Y. (1968). (f) E. G. Rozantsev, *Free Nitroxyl Radicals*, Plenum Press, New York, N.Y. (1970). (g) L. B. Volodarsky, *Imidazoline Nitroxides*, CRC Press Inc., Boca Raton (1988). (h) E. Breuer, H. G. Aurich and A. Nielsen, *Nitrones, Nitronates, and Nitroxides*, John Wiley and Sons, Chichester UK (1989). (i) L. B. Volodarsky, V. A. Reznikov and V. I. Ovcharenko, *Synthetic Chemistry of Stable Nitroxides*, CRC Press inc., Boca Raton (1994). (j) N. Kocherginsky and H. M. Swartz, *Nitroxide Spin Labels: Reactions in Biology and Chemistry* CRC Press Inc., Boca Raton (1995). (k) A. Alberti (editor), *Nitroxide Radicals and Nitroxide Based High-Spin Systems*, Series: Landolt-Boernstein, Group 2, Subvolume D, Springer Verlag, New York N.Y. (2005). (l) G. I. Likhtenshtein, J. Yamauchi, S. Nakatsuji, A. I. Smirnov and R. Tamura, *Nitroxides: Applications in Chemistry, Biomedicine, and Materials Science*, Wiley-VCH Verlag GmbH Weinheim, (2008). (m) N. Naik, R. Braslau, *Tetrahedron*, 54, 667-696, (1998). (n) L. B. Volodarsky, A. Ya. Tikhonov, *Synthesis*, 704-715 (1986). (o) H. Karoui, F. Le Moigne, O. Ouari, P. Tordo, In "*Stable radicals: fundamentals and applied aspects of odd-electron compounds*" Nitroxides Radicals: Properties, Synthesis, and Applications; Wiley VCH, R. Hicks Ed., 174-229 (2010).

In the following more specific embodiments of the invention, the compound 4,4-ureylene-di-(2,2,6,6-tetramethylpiperidinyloxyl (also designated as "bTUrea")

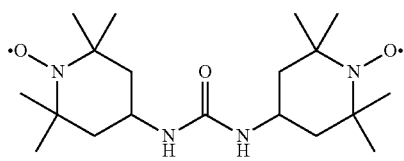

is, of course, always excluded.

Preferred groups $Q_1$ and $Q_2$ consisting of a nitroxide-containing 5- to 8-membered heterocyclic ring, which may contain an additional heteroatom or heteroatomic group selected from O, S, N$^+$—O$^-$, NH, N(C$_{1-6}$ alkyl) wherein the alkyl is straight, branched or cyclic, and may contain one double bond and is substituted at least at all positions alpha to the (N—O.) group, are selected from the following groups without restriction to any specific embodiments of the invention.

$Q_a$:

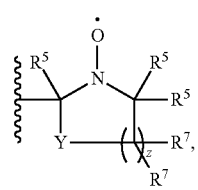

$Q_b$:

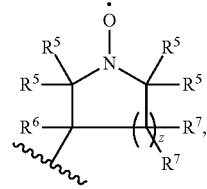

$Q_c$:

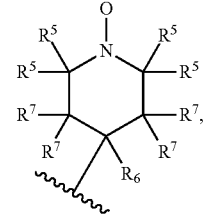

wherein $R^5$ in each instance is independently a substituted or unsubstituted linear, branched or cyclic $C_1$-$C_6$ alky group; a substituted or unsubstituted linear, branched or cyclic group heteroaliphatic group comprising 5 C atoms and one heteroatom selected from O, S, or N($R^{12}$); substituted or unsubstituted aryl; or substituted or unsubstituted heteroaryl; or wherein two geminal $R^5$'s are joined to form together with the secondary C atom to which they are bound a further substituted or otherwise unsubstituted cyclopentane or cyclohexane ring or a further substituted or otherwise unsubstituted saturated 5- or 6-membered heterocyclic ring comprising one atom or group selected from —O—, —S—, —N($R^{12}$)—, —P(O)OH—, —P(O)(C$_{1-6}$ alkyl) and —P(O)(C$_{1-6}$alkoxy); and Y is selected from —O—, —S—, —N($R^{12}$)— or —C($R^6$)$_2$—;

and, preferably, all $R^5$s are identical and are selected from unsubstituted linear or branched $C_1$-$C_6$ alkyl, or both germinal groups $R^5$ are joined to form together with the secondary C atom to which they are bound two identical rings selected from a cyclopentane or cyclohexane ring or a tetrahydrofurane or tetrahydroprane ring which rings may bear further on or more substituents selected from the substituents mentioned above in the context of the definition of alkyl groups and heterocycic rings, respectively without restriction to any specific embodiments of the invention;

$R^{12}$ is as defined above;

$R_6$ and $R_7$ are each independently selected from hydrogen, hydroxyl; $C_{1-6}$ alkyloxy; thiol; $C_{1-6}$ alkylthio; N(R')R"), wherein R' and R" are independently $R^{12}$; nitro; halo; cyano; azido; substituted or unsubstituted linear, branched or cyclic $C_1$-$C_6$ alkyl; a substituted or unsubstituted linear, branched or cyclic group heteroaliphatic group comprising 5 C atoms and one heteroatom or hetero group, respectively, selected from O, S, N($R^{11}$), P($R^{12}$), P(=O)OH and P(=O)O(C$_{1-6}$ alkyl); substituted or unsubstituted aryl, substituted or unsubstituted heteroaryl, $C_{1,6}$ alklycarbonyl; $C_{1-6}$ alkyl sulfonyl; $C_{1-6}$ alkyl sulfinyl; substituted or unsubstituted aryl sulfinyl; or substituted or unsubstituted aryl sulfonyl; with $R_6$ preferably being hydrogen in all embodiments of the invention;

z is 1 or 2; and denotes the point of attachment of the heterocyclic ring to the nitrogen atom, the group X or the group M of formula (I) by a single bond.

$Q_d$:

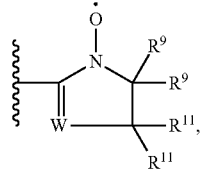

$Q_e$:

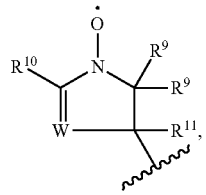

$Q_f$:

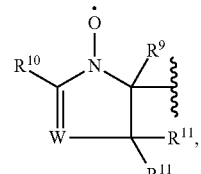

wherein $R^9$ is as defined for $R^5$ above, $R^{12}$ is as defined above;

$R^{10}$ is a substituted or unsubstituted linear, branched or cyclic $C_1$-$C_6$ alky group; a substituted or unsubstituted linear, branched or cyclic group heteroaliphatic group comprising 5 C atoms and one heteroatom selected from O, S, or $N(R^{12})$; substituted or unsubstituted aryl; or substituted or unsubstituted heteroraryl;

$R^{11}$ is in each instance independently selected from hydrogen, hydroxyl; $C_{1-6}$ alkyloxy; thiol; $C_{1-6}$ alkylthio; $N(R')R''$), wherein R' and R'' are independently $R^{12}$; nitro; halo; cyano; azido; substituted or unsubstituted linear, branched or cyclic $C_1$-$C_6$ alkyl; a substituted or unsubstituted linear, branched or cyclic group heteroaliphatic group comprising 5 C atoms and one heteroatom or hetero group, respectively, selected from O, S, $N(R^{11})$, $P(R^{12})$, $P(=O)OH$ and $P(=O)O(C_{1-6}$ alkyl); substituted or unsubstituted aryl, substituted or unsubstituted heteroaryl, $C_{1,6}$ alklycarbonyl; $C_{1-6}$ alkyl sulfonyl; $C_{1-6}$ alkyl sulfinyl; substituted or unsubstituted aryl sulfinyl; or substituted or unsubstituted aryl sulfonyl; and is preferably hydrogen when attached to the C atom which also forms the single bond by which the group $Q_e$ is attached to the nitrogen atom, the group X or the group M of formula (I);

W is N or $N^+$—$O^-$; and

denotes the point of attachment of the heterocyclic ring to the nitrogen atom, the group X or the group M of formula (I) by a single bond;

$Q_g$:

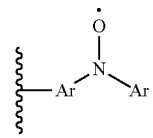

$Q_h$:

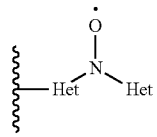

$Q_i$:

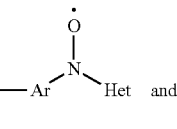

and $Q_j$:

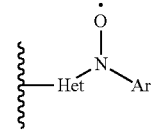

wherein

Ar is independently in each instance substituted or unsubstituted aryl, and Het is independently in each instance substituted or unsubstituted heteroaryl; and denotes the point of attachment of the aryl group or the heteroaryl group to the nitrogen atom, the group X or the group M of formula (I) by a single bond;

The nitroxide-containing groups $Q_1$ and $Q_2$ are attached to $NR^1$, $X(=C=O$ or $SO_2)$ or M ($=O$ or $NR^2$) via one of their C atoms. Exemplary synthetic procedures for this are shown in the Examples.

In embodiments of the invention, in the compound of formula (I)

M is $NR_2$; and $R_2$ is hydrogen; or, if X is CO, a is 1 and M is $NR_2$, $R_1$ and $R_2$ together form a bridging —$CH_2CHG$- or —$CH_2CH_2CHG$- or —$CH_2CH(G)CH_2$— group with G=$(CH_2)_o$-E, wherein o is an integer of from 0 to 10 and E is: COOH, OH, $NH_2$, $N_3$, C≡CH or $SSO_2Me$; or $(CH_2-CH_2-O)_m$—$CH_3$, wherein m is an integer of from 1 to 500 or a bridging group $CH_2CH_2$—, —CH2—CHOH—$CH_2$— or —$CH_2CH_2CH_2$—; and $Q_1$ and $Q_2$ are independently selected from $Q_a$ to $Q_c$ as defined above, or $Q_1$ and $Q_2$ are be independently selected from

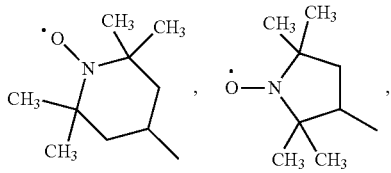

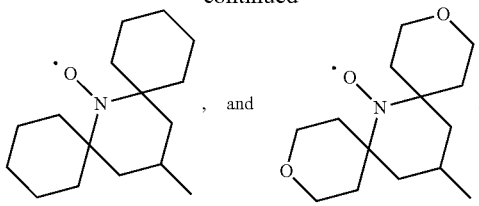, and

In other embodiments of the invention, in the compound of formula (I)

a is 1, when X is SO₂; and 0 or 1, when X is CO;

M is NR₂; and

R₂ is hydrogen;

R₁ is H; $(CH_2)_o$-E, wherein o is an integer of from 1 to 10 and E is COOH; or $(CH_2-CH_2-O)_m-CH_3$ or $(CH_2-CH_2-O)_m-H$, wherein m is an integer of from 1 to 500; or

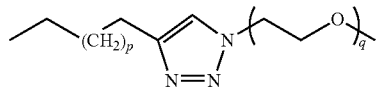

wherein p is an integer of from 0 to 7 and q is an integer of from 1 to 500; or if X is CO, a is 1 and M is NR₂, R₁ and R₂ together form a bridging CH₂CHG- or —CH₂CH₂CHG- or —CH₂CH(G)CH₂— group with G=$(CH_2)_o$-E, wherein o is an integer of from 0 to 10 and E is: COOH, OH, NH₂, N₃, C≡CH or SSO₂Me; or $(CH_2-CH_2-O)_m-CH_3$, wherein m is an integer of from 1 to 500; or, alternatively, if X is CO, a is 1 and M is NR₂, R₁ and R₂ together form a bridging CH₂CH₂—, —CH2—CHOH—CH₂— or —CH₂CH₂CH₂— group;

and Q₁ and Q₂ are independently selected from $Q_u$ to $Q_c$ as defined above, or Q₁ and Q₂ are independently selected from

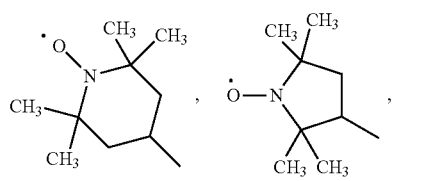

Preferably, in the above embodiment,

X is CO;

a is 1;

R₁ is H; or $(CH_2-CH_2-O)_m-CH_3$ or $(CH_2-CH_2-O)_m-H$, wherein m is an integer of from 1 to 500, preferably 1 to 15; or

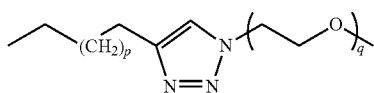

wherein p is an integer of from 0 to 7 and q is an integer of from 1 to 500; or

R₁ and R₂ together form a bridging group —CH₂CH(G)CH₂— wherein G is $(CH_2-CH_2-O)_m-CH_3$ with m being an integer of from 1 to 500, preferably 1 to 15, or a bridging —CH₂CH₂—, —CH₂—CHOH—CH₂— or —CH₂CH₂CH₂— group;

and

Q₁ and Q₂ are selected from

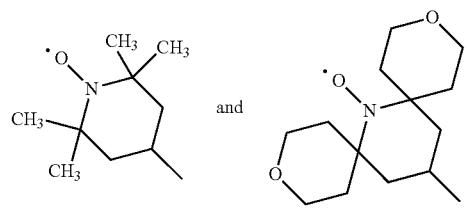

In embodiments of the invention, Q₁ and Q₂ are identical. Most preferably, they are both

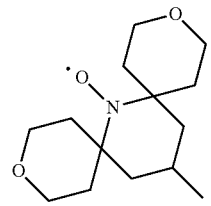

In all of the above embodiments, m in $(CH_2-CH_2-O)_m-CH_3$ or $CH_2-CH_2-O)_m-H$ is preferably an integer of from 1 to 200, more preferred 1-100, and even more preferred 1-20 or 1-15.

Presently preferred compounds of claim 1 are:

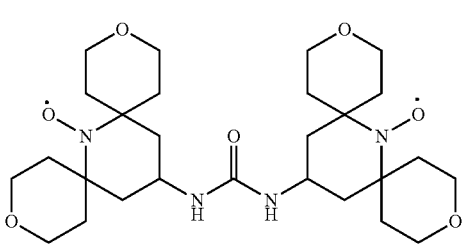

(15-{[(7oxyl-3,11-dioxa-7-azadispiro[5.1.5.3]hexadec-15-yl)carbamoyl]amino}-[3,11-dioxa-7-azadispiro[5.1.5.3]hexadec-7-yl])oxidanyl), designated as "bPyTurea" or "PyPol";

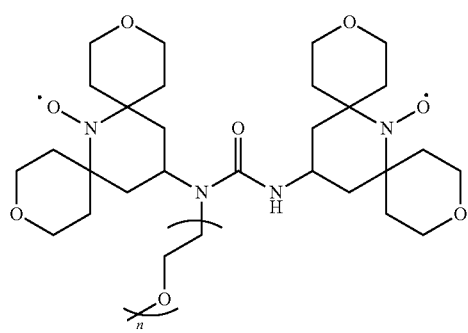

57 n = 2
58 n = 4

57: (15-{[(7-oxyl-3,11-dioxa-7-azadispiro[5.1.5.3]hexadec-15-yl)carbamoyl][2-(2-methoxyethoxy)ethyl]amino}-[3,11-dioxa-7-azadispiro[5.1.5.3]hexadec-7-yl])oxidanyl, designated as "bPyTureaPEG2";

58: (15-{[(7-oxyl-3,11-dioxa-7-azadispiro[5.1.5.3]hexadec-15-yl)carbamoyl][2-(2,5,8,11-tetraoxatridecan-13-ylamino)}-[3,11-dioxa-7-azadispiro[5.1.5.3]hexadec-7-yl])oxidanyl designated as "bPyTureaPEG4" or "AMUPOL";

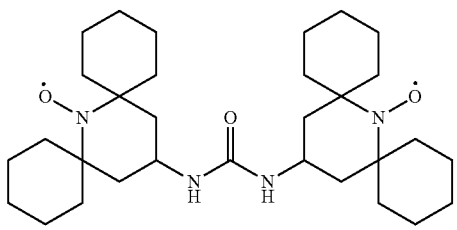

53

(15-{[(7oxyl-7-azadispiro[5.1.5.3]hexadec-15-yl)carbamoyl]amino}-7-azadispiro[5.1.5.3]hexadec-7-yl)oxidanyl, designated as "bCTurea";

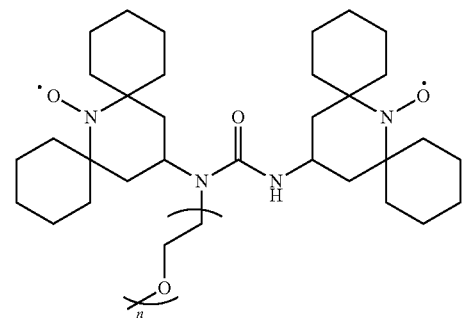

54 n = 2
55 n = 4

54: (15-{[(7-hydroxy-7-azadispiro[5.1.5.3]hexadec-15-yl)carbamoyl][2-(2-methoxyethoxy) ethyl]amino}-7-azadispiro[5.1.5.3]hexadec-7-yl)oxidanyl, designated as "bCTureaPEG2";

55. (15-{[(7-oxyl-7-azadispiro[5.1.5.3]hexadec-15-yl) carbamoyl][2-(2-methoxyethoxy) ethyl]amino}-7-azadispiro[5.1.5.3]hexadec-7-yl)oxidanyl, designated as "bCTureaPEG4";

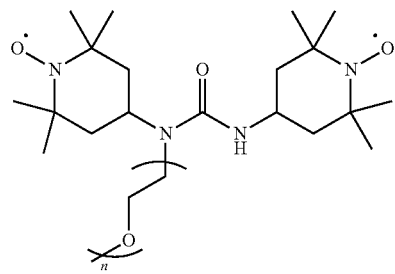

51 n = 2
52 n = 4

51: (4-{[2-(2-methoxyethoxy)ethyl][(1-oxyl-2,2,6,6-tetramethylpiperidin-4-yl)carbamoyl]amino}-2,2,6,6-tetramethylpiperidin-1-yl)oxidanyl, designated as "bTureaPEG2";

52: (4-{(2,5,8,11-tetraoxatridecan-13-yl)[(1-oxyl-2,2,6,6-tetramethyl piperidin-4-yl)carbamoyl]amino}-2,2,6,6-tetramethylpiperidin-1-yl)oxidanyl, designated as "bTureaPEG4";

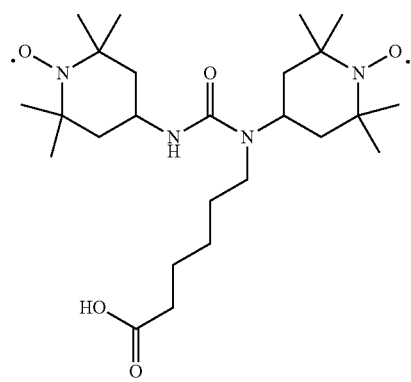

59

(4-{(5-carboxypentyl)[(1-oxyl-2,2,6,6-tetramethylpiperidin-4-yl)carbamoyl]amino}-2,2,6,6-tetramethylpiperidin-1-yl)oxidanyl;

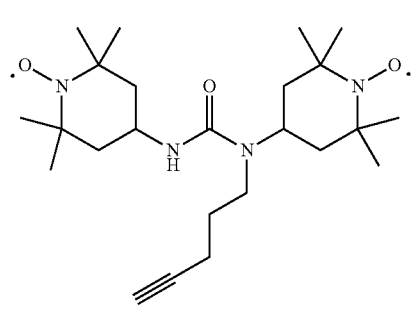

60

(4-{(pent-4-yn-1-yl)[(1-oxyl-2,2,6,6-tetramethylpiperidin-4-yl)carbamoyl]amino}-2,2,6,6-tetramethylpiperidin-1-yl)oxidanyl;

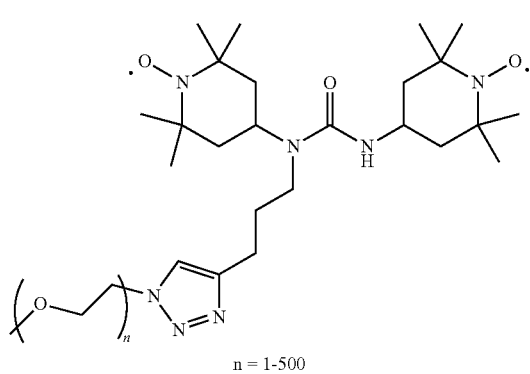

n = 1-500

(4-{3-[1-(PEG)-1H-1,2,3-triazol-4-yl]propyl}[(1-oxyl-2,2,6,6-tetramethylpiperidin-4-yl)carbamoyl]amino}-2,2,6,6-tetramethylpiperidin-1-yl)oxidanyl,
 designated as "bTureaPEG500", when n=500;

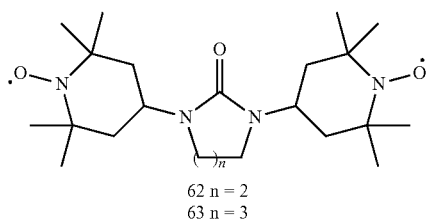

62 n = 2
63 n = 3

62: 1,3-bis(1-oxyl-2,2,6,6-tetramethylpiperidin-4-yl)imidazolidin-2-one,
 designated as "bTureaC5";
63: 1,3-bis(1-oxyl-2,2,6,6-tetramethylpiperidin-4-yl)tetrahydropyrimidin-2(1H)-one,
 designated as "bTureaC6";

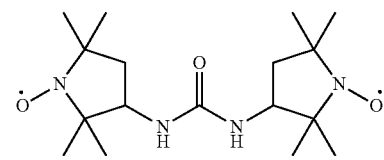

(3-{[(1-oxyl-2,2,5,5-tetramethylpyrrolidin-3-yl)carbamoyl]amino}-[2,2,5,5-tetramethylpyrrolidin-3-yl])oxidanyl,
 designated as "bProxurea";

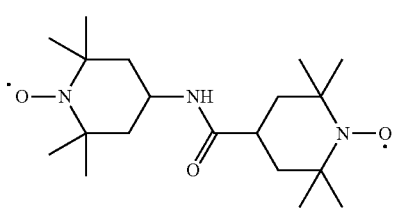

(4-{[(1-oxyl-2,2,6,6-tetramethylpiperidin-4-yl)carbonyl]amino}-2,2,6,6-tetramethylpiperidin-1-yl)oxidanyl,
 designated as "bTamide";

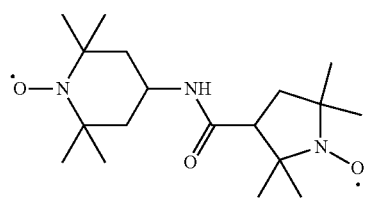

{3-[(1-oxyl-2,2,6,6-tetramethylpiperidin-4-yl)carbamoyl]-2,2,5,5-tetramethylpyrrolidin-1-yl}oxidanyl,
 designated as "ProxTamide";

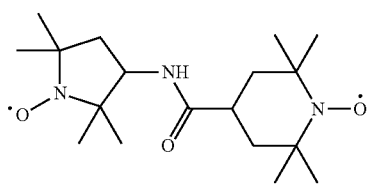

(3-{[(1-oxyl-2,2,6,6-tetramethylpiperidin-4-yl)carbonyl]amino}-2,2,5,5-tetramethylpyrrolidin-1-yl)oxidanyl,
 designated as "TProxamide";

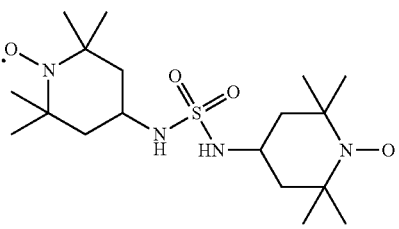

(4-{[(1-oxyl-2,2,6,6-tetramethylpiperidin-4-yl)sulfamoyl]amino}-2,2,6,6-tetramethylpiperidin-1-yl)oxidanyl;

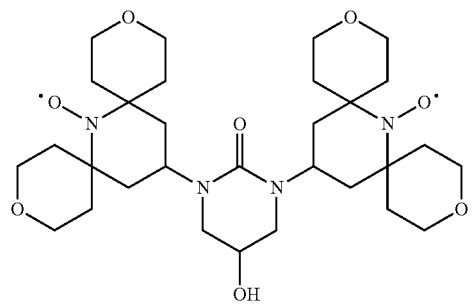

5-hydroxy-1,3-bis(7-oxyl-3,11-dioxa-7-azadispiro[5.1.5.3]hexadec-15-yl)tetrahydropyrimidin-2(1H)-one;
 designated as "PyPOLC6OH";

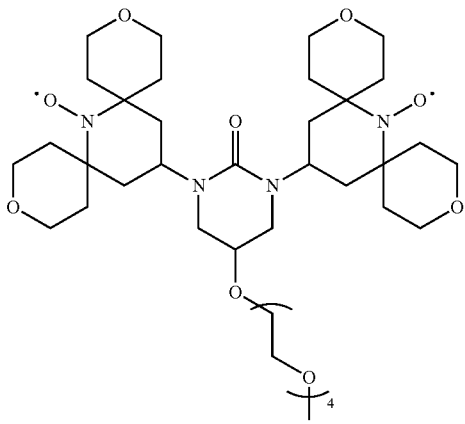

1,3-bis(7-oxyl-3,11-dioxa-7-azadispiro[5.1.5.3]hexadec-15-yl)-5-(2,5,8,11-tetraoxatridecan-13-yloxy)tetrahydropyrimidin-2(1H)-one;

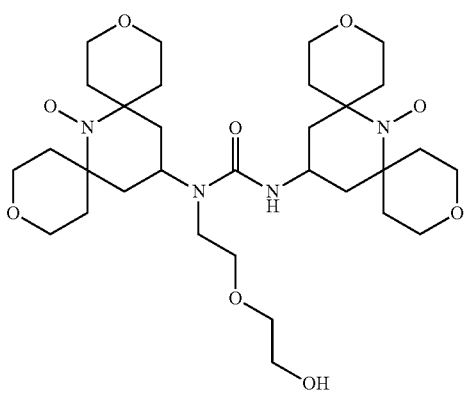

(15-{[(7-oxyl-3,11-dioxa-7-azadispiro[5.1.5.3]hexadec-15-yl)carbamoyl][2-(2-hydroxyethoxy)ethyl]amino}-[3,11-dioxa-7-azadispiro[5.1.5.3]hexadec-7-yl])oxidanyl, designated as "PyPOLPEG2OH"; and

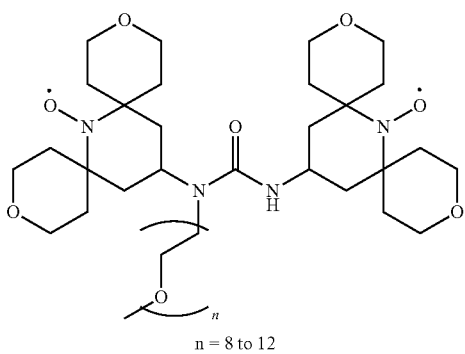

n = 8 to 12

α-{(7-oxyl-3,11-dioxa-7-azadispiro[5.1.5.3]hexadec-15-yl)[(7-oxyl-3,11-dioxa-7-azadispiro[5.1.5.3]hexadec-15-yl)carbamoyl]amino}ω-methylpoly(ethane-1,2-diyloxy), designated as "PyPOLPEG10".

The syntheses of these compounds are described in the Examples.

The compounds of the invention generally are very stable and have a good to very good water solubility.

The biradical compounds of the invention can be used as a Dynamic Nuclear Polarization (DNP) agents for polarizing an NMR-active spin of a nucleus of an analyte in Nuclear Magnetic Resonance (NMR) spectroscopy. An NMR-active spin is spin half or uneven multiples thereof. The term NMR spectroscopy, as used herein, encompasses Solid State NMR (SS-NMR) spectroscopy, liquid state NMR spectroscopy and Magnetic Resonance Imaging (MRI), in all of which the biradical compounds of the invention may be used as DNP agents.

The term analyte, as used herein, denotes a chemical or biological entity, such as a solid inorganic, organic or metallo-organic material having an crystal lattice or an amorphous solid structure, e.g. zeolithes, nanoparticles, mesoporous and porous materials, glasses, Metal Organic Frameworks (MOF's), a molecular chemical or biochemical compound including polymeric compounds and macromolecular compounds, e.g., proteins, enzymes, DNA/RNA, and a biological entity, e.g. a whole cell, a leaf, a virus particle, tissue or bone components or a whole body, having one or more NMR-active spins to be investigated by NMR spectroscopy. The molecular chemical or biochemical compound may be an isolated inorganic, organic, metallo-organic or biochemical compound or an inorganic, organic or biochemical compound in its natural biological environment. The analyte may be dissolved in an aqueous medium, an organic solvent or solvent mixture or an aqueous/organic solvent mixture, or it may be present without a solvent.

The investigation by NMR spectroscopy could e.g. be structure determination, monitoring of reaction kinetics, or flow imaging.

The nucleus having an NMR-active spin may be any known such nucleus, e.g. $^1$H, $^2$H, $^6$Li, $^7$Li, $^{10}$B, $^{11}$B, $^{13}$C, $^{14}$N, $^{15}$N, $^{17}$O, $^{19}$F, $^{23}$Na, $^{25}$Mg, $^{27}$Al, $^{29}$Si, $^{31}$P, $^{33}$S, $^{35}$Cl, $^{37}$Cl, $^{39}$K, $^{41}$K, $^{43}$Ca, $^{47}$Ti, $^{49}$Ti, $^{50}$V, $^{53}$Cr, $^{77}$Se, $^{89}$Y, $^{117}$Sn, and $^{199}$Hg.

The DNP agent may be dissolved in the solvent of the analyte or can be introduced without a solvent chemically bound to the analyte, such as in doped polymers, materials functionalized with polarizing agents, or paramagnetic spin labels on biological samples. The polarizing agent could also be dispersed in the analyte, for example by initially introducing the polarizing agent with a solvent and evaporating the solvent in a following step leaving the polarizing agent and analyte, or be introduced by wet impregnation. The polarizing agent could also be added during a synthetic preparation step.

The polarizing agent may be present in a solid state during the polarization time, such as in a frozen solution comprising a frozen solvent or solvent mixture containing the analyte or in a solid state without solvent.

In other embodiments, the DNP agent may be present in a liquid state or in a liquid solution during the polarization time.

Use concentration of the DNP agent concentration may be in the range of from about 1 to about 200 mM.

In solid state NMR experiments, the temperature of a sample containing the analyte and the DNP agent is usually in the range of from about 1 to about 200 K.

The polarization time during which microwave irradiation is applied to the electron spins and the nuclear spins are polarized via transfer of the polarization can be continuous (microwaves are on all the time) and simultaneous with the NMR spectroscopic measurement time. Alternatively, the microwave irradiation can be pulsed, or a combination of short and long pulses. Microwave irradiation can also occur as a step before the NMR spectroscopy, for example in dissolution DNP or temperature jump DNP, where a solid DNP sample is polarized in the solid state and then melted for solution state applications. In the case of continuous microwave irradiation the polarization builds up with an exponential time constant (Tpol) which can be measured similarly to T1 measurements in NMR experiments.

The frequency range of the microwave irradiation by which the polarization is transferred to an NMR-active nucleus is usually from about 5 to about 800 GHz.

The experimental setup may be either static or spinning samples.

The compounds of the invention show high DNP efficiencies.

Table 1 shows the 1H DNP signal enhancement and polarization build-up time at two DNP frequencies of selected compounds of the invention.

TABLE 1

| Biradical Compound No. | Solubility in Glycerol/H$_2$O (60/40) | 263 GHz T$_{pol}$ | 263 GHz DNP ε | 395 GHz T$_{pol}$ | 395 GHz DNP ε |
|---|---|---|---|---|---|
| 58 | ~25 mM | 3.4 s | 235 | 4.9 s | 128 |
| 57 | ~25 mM | 4.9 s | 217 | 6.4 s | 123 |
| 56 | ~25 mM | 5.7 s | 207 | 8.7 s | 128 |
| 61 | ~20 mM | 3.0 s | 116 | 3.7 s | 61 |
| 51 | ~10 mM | 5.6 s | 120 | 7.7 s | 81 |
| 52 | ~10 mM | | 120 | | |
| 69 | >10 mM | | 290 | | 160 |
| 70 | >10 mM | | 278 | | 138 |
| 71 | >20 mM | | 303 | | |
| 72 | >20 mM | | 257 | | |
| bTUrea (4,4-ureylene-di-(2,2,6,6-tetramethyl-piperidinyloxyl) | ~3 mM | 16.5 | 62 | | |
| TOTAPOL | | 5.6 s | 75 | 7.7 s | 30 |

The 1H DNP signal enhancement (DNP ε) was measured at 9.4 T 263 GHz and 14.1 T 395 GHz at 97 K sample temperature and 8 kHz magic angle spinning (MAS) frequency for Compounds 58, 57, 56, 61 and 51 according to the invention compared to TOTAPOL. All samples were prepared with 10 mM biradical polarizing agent, 0.25 M 13C-15N Proline, in glycerol-d8/D2O/H2O (60/30/10% volume ratio). The 1H DNP signal enhancement was measured via 1H-13C cross polarization experiment with and without microwave irradiation. Polarization build-up time, Tpol, was measured with saturation recovery experiment with microwave irradiation on continuously.

FIG. 1 shows a DNP experiment with Compound 58 ((15-{[(7-oxyl-3,11-dioxa-7-azadispiro[5.1.5.3]hexadec-15-yl)carbamoyl][2-(2,5,8,11-tetraoxatridecan-13-ylamino)}-[3,11-dioxa-7-azadispiro[5.1.5.3]hexadec-7-yl])oxidanyl, designated as "bPyTureaPEG4" or "AMUPOL") as a polarizing agent at 14.1 T, 600 MHz 1H frequency, 395 GHz microwave frequency. 1H-13C CPMAS experiment at 14 kHz MAS, 100 K sample temperature, 8 scans signal averaging, 1 dummy scan, 6.4 s recycle delay. Top trace (DNP) with microwave irradiation and bottom trace (no DNP) without microwave. Concentration: 10 mM of Compound 58, 0.25 M 13C-15N Proline in glycerol-d8/D2O/H2O (60/30/10% volume ratio).

EXAMPLES

General Procedures

All chemicals used in synthesis were purchased from Aldrich Chemical Co. Commercially available starting materials were used without further purification. Purification of products was accomplished by flash column chromatography on silica gel (Merck silica gel 60, 230-400 mesh) and neutral alumina (Merck Aluminium oxide 90 active neutral, 70-230 mesh). NMR measurements were recorded on a Bruker AVL 300 spectrometer ($^1$H-NMR 300.1 MHz and $^{13}$C-NMR 75.5 MHz) using CDCl$_3$ as the solvent (internal reference). Splitting patterns are indicated as follows: br, broad; s, singlet; d, doublet; t, triplet; q, quartet; m, multiplet; dd, doublet of doublets; dt, doublet of triplets. Mass spectral analyses were carried out using a Q-STAR Elite at the Aix Marseille Université Mass Spectrum Facility, Spectropole Saint Jérôme Marseille. Melting points were determined using a Büchi B-540 apparatus and were uncorrected. The final products were purified to ≥95% and were confirmed by HPLC and/or elemental analysis. HPLC experiments were performed using Agilent 1200 system equipped with UV-Vis absorption and fluorescence detectors. A fused core C18 column (Phenomenex, Kinetex C18, 100 mm×4.6 mm, 2.6 μm) was used. Typically, a gradient elution using aqueous mobile phase with increasing fraction of acetonitrile (from 10% to 40% over 5 min and from 40 to 100% over 5 min) in the presence of 0.1% TFA was used. The compounds were eluted using a flow rate of 1.5 ml/min.

Example 1

Synthesis of (15-{[(7-Oxyl-3,11-dioxa-7-azadispiro [5.1.5.3]hexadec-15-yl)carbamoyl]amino}-[3,11-dioxa-7-azadispiro[5.1.5.3]hexadec-7-yl])oxidanyl (Compound 56)

1.A. Synthesis of Compound 3 (General Procedure A)

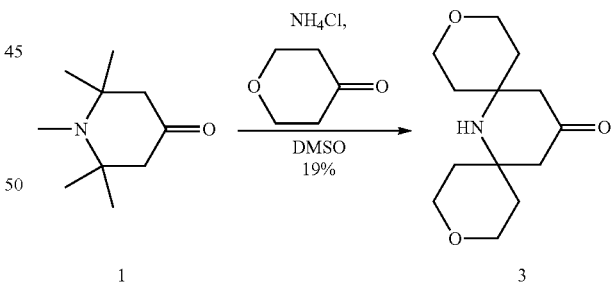

To a stirred mixture of 1,2,2,6,6-pentamethypiperidin-4-one 1 (6.08 g, 0.036 mol) and tetrahydro-4H-pyran-4-one (10.8 g, 0.108 mol) in dimethylsulfoxide (70 mL), NH$_4$Cl (11.55 g, 0.216 mol) was added at room temperature. The mixture was heated at 80° C. during 24 h, then it was diluted with water (200 mL), acidified with 1N HCl aqueous solution (40 mL) and the mixture was extracted with diethylether (3×100 mL). The aqueous layer was adjusted to pH 11 by adding 50 mL of 10% K$_2$CO$_3$ aqueous solution and then extracted with chloroform (2×100 mL). The organic phase was concentrated under reduced pressure, diluted in ethylacetate (100 mL), washed with brine (100 mL), dried over Na$_2$SO$_4$, and the solvent was distilled under reduced pressure. The crude product was purified by SiO$_2$ column chromatography with AcOEt/pentane (1/1) and recrystallized to afford 7-aza-3,11-dioxadispiro[5.1.5.3]hexadecane-15-one 3 (2.00 g, 23%) as a white solid. mp: 170° C. (lit. mp: 167° C.) $^1$H NMR (CDCl$_3$) δ1.64; (t, 8H, J=5.6 Hz), 2.41; (s, 4H), 3.54-3.60; (m, 4H), 3.82-3.88; (m, 4H). $^{13}$C NMR (CDCl$_3$) δ40.24, 51.86, 54.59, 63.46, 208.95. HRMS-ESI: calcd for C$_{13}$H$_{21}$NO$_3$ [M+H]$^+$ 240.1594, found 240.1594.

1.B. Synthesis of Compound 5 (General Procedure B)

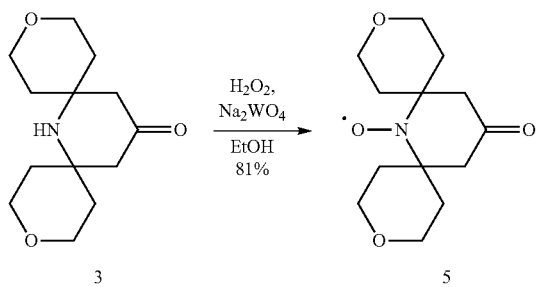

Compound 3 (2.9 g, 12.1 mmol) and Na$_2$WO$_4$.2H$_2$O (400 mg, 1.21 mmol) were stirred in ethanol (100 mL). H$_2$O$_2$ (35%, 48.4 mmol, 5 mL) was added and the mixture was stirred for 24 h at room temperature. At the end of reaction, K$_2$CO$_3$ was added and the solution was extracted twice with chloroform (100 mL). The organic layer was dried over Na$_2$SO$_4$ and distilled under reduced pressure. The crude product was purified by column chromatography (SiO$_2$, DCM:EtOH) to provide (15-oxo-3,11-dioxa-7-azadispiro [5.1.5.3]hexadec-7-yl)oxidanyl 5 as a yellow solid (2.5 g, 81%). mp: 148.5° C. (lit. mp: 149.5° C.) ESI-MS m/z=255 [M+H]$^+$; 277 [M+Na]$^+$.

1.C. Synthesis of Compound 7 (General Procedure C)

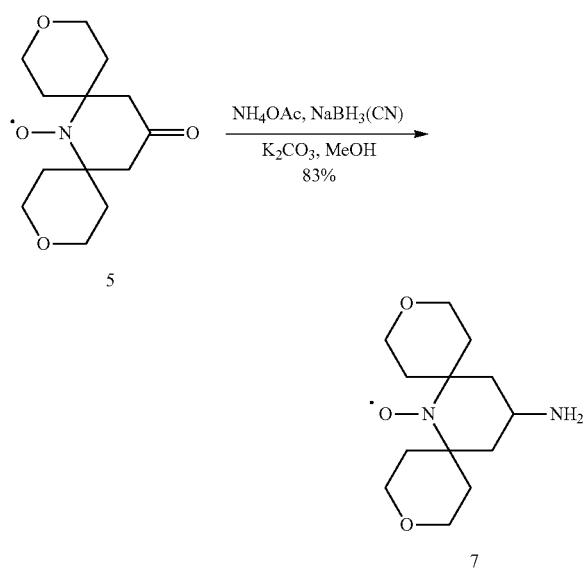

Under Argon atmosphere, a solution of ammonium acetate (2.55 g, 33 mmol) in MeOH (25 ml) was stirred for 5 min at rt. K$_2$CO$_3$ was added to adjust the pH at 8. Then a solution of 5 (840 mg, 3.3 mmol) in MeOH was added and the reaction mixture was stirred at rt. NaBH(CN)$_3$ (540 mg, 8.6 mmol) was added in one portion. The reaction was stirred 16 h at rt and 5 ml of sat. NaHCO$_3$ were added. MeOH was removed under reduced pressure and the remaining aqueous phase was extracted twice with chloroform. The organic layer was dried on Na$_2$SO$_4$, solvent removed under vacuum and the residue was column chromatographied to give (15-amino-3,11-dioxa-7-azadispiro[5.1.5.3]hexadec-7-yl)oxidanyl 7 (700 mg, 2.743 mmol, 83%) as a red solid. mp: 140.5° C. HRMS-ESI: m/z calcd for C$_{13}$H$_{23}$N$_2$O$_3$* [M+H]$^+$ 256.1781, found 256.1781

1.D. Synthesis of Compound 56 (General Procedure D)

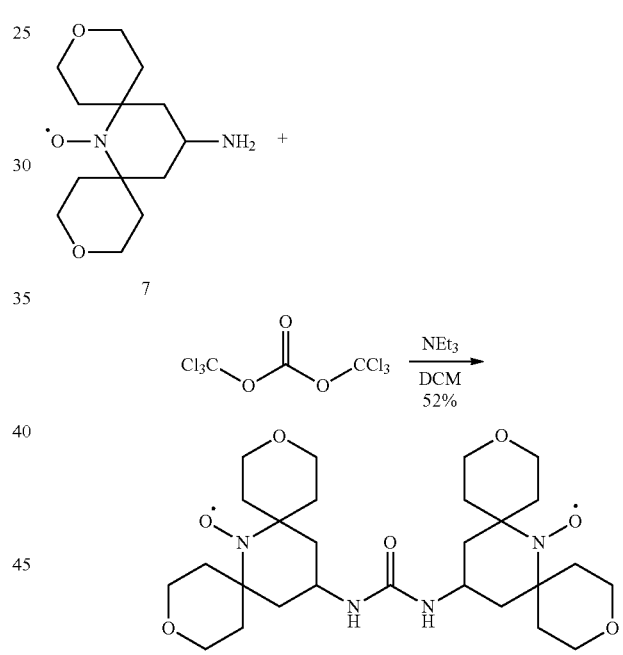

To a solution of 7 (200 mg, 0.78 mmol) and NEt$_3$ (220 μl, 1.56 mmol) in DCM (5 ml) was added a solution of triphosgene (38 mg, 0.13 mmol) in DCM and the solution was stirred at it for 6 h. A solution of sat. NaHCO$_3$ is added and the mixture is extracted with DCM twice. The organic phase was dried on Na$_2$SO$_4$, solvent removed under vacuum and the residue was column chromatographied to afford (15-{[(7oxyl-3,11-dioxa-7-azadispiro[5.1.5.3]hexadec-15-yl)carbamoyl]amino}-3,11-dioxa-7-azadispiro[5.1.5.3]-hexadec-7-yl)oxidanyl 56 as a red solid (100 mg, 0.18 mmol, 52%. HRMS-ESI: m/z calcd for C$_{27}$H$_{44}$N$_4$O$_7$** [M+H]$^+$ 537.3283, found 537.3283. Elemental analysis: found C, 53.82; H. 7.63; N, 8.89 calcd for C$_{27}$H$_{44}$N$_4$O$_7$+ 1.05 CH$_2$Cl$_2$: C, 53.81; H, 7.42; N, 8.95.

Example 2

Synthesis of (15-{[(7-Oxyl-3,11-dioxa-7-azadispiro[5.1.5.3]hexadec-15-yl)carbamoyl][2-(2-methoxyethoxy)ethyl]amino}-[3,11-dioxa-7-azadispiro[5.1.5.3]hexadec-7-yl])oxidanyl (Compound 57);

and

Example 3

(15-{[(7-Oxyl-3,11-dioxa-7-azadispiro[5.1.5.3]hexadec-15-yl)carbamoyl][2-(2,5,8,11-tetraoxatridecan-13-ylamino)}-[3,11-dioxa-7-azadispiro[5.1.5.3]hexadec-7-yl])oxidanyl (Compound 58)

2.A. and 3.A. Syntheses of Compounds 10 and 11 (General Procedure E)

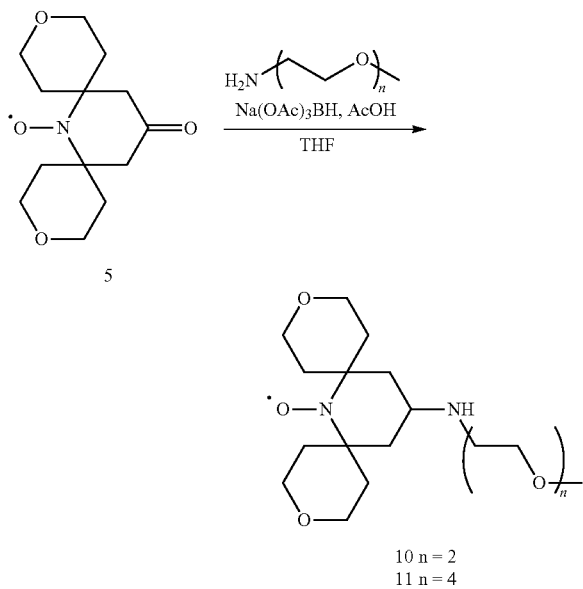

A solution of 5 (500 mg, 1.97 mmol), tetra(ethylene glycol) methyl ether amine (370 mg, 1.79 mmol) and AcOH (0.6 ml) in THF (30 ml) was stirred at rt for 2 h. Na(OAc)$_3$BH (1.40 g, 5.4 mmol) was added and the reaction was stirred at rt for 12 h. THF was removed under reduced pressure and the residue was solubilized in DCM. The organic phase was washed with a saturated solution of NaHCO$_3$. The aqueous phase is saturated with NaCl and extracted with chloroform twice. The organic phases are dried (Na$_2$SO$_4$) and solvents are removed under reduced pressure. The residue is purified by column chromatography to give [15-{(2,5,8,11-tetraoxatridecan-13-yl)amino}-3,11-dioxa-7-azadispiro[5.1.5.3]-hexadec-7-yl]oxidanyl 11 (540 mg, 1.22 mmol, 68%) as a red oil. HRMS-ESI: m/z calcd C$_{22}$H$_{41}$N$_2$O$_7$* [M+H]$^+$ 446.2987, found 446.2986

The same procedure was used to synthesize (15-{[2-(2-methoxyethoxy)ethyl]amino}-3,11-dioxa-7-azadispiro[5.1.5.3]hexadec-7-yl)oxidanyl 10, starting from di(ethylene glycol) methyl ether amine. ESI-HRMS: m/z calcd C$_{18}$H$_{33}$N$_2$O$_5$* [M+H]$^+$ 358.2462, found 358.2462

2.B. and 3.B. Syntheses of Compounds 57 and 58 (General Procedure F)

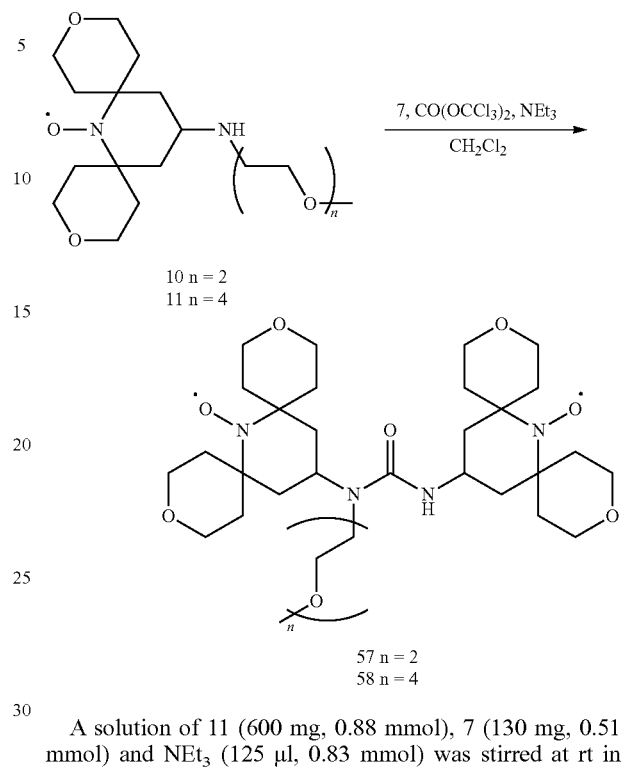

A solution of 11 (600 mg, 0.88 mmol), 7 (130 mg, 0.51 mmol) and NEt$_3$ (125 µl, 0.83 mmol) was stirred at rt in DCM (5 ml) for 6 h. The solution was washed with brine, dried over Na$_2$SO$_4$ and the solvent was removed under vacuum. The residue was purified using flash chromatography to give (15-{[(7-oxyl-3,11-dioxa-7-azadispiro[5.1.5.3]hexadec-15-yl)carbamoyl][2-(2,5,8,11-tetraoxatridecan-13-ylamino)}-[3,11-dioxa-7-azadispiro-[5.1.5.3]hexadec-7-yl])oxidanyl 58 as a red oil (120 mg, 0.16 mmol, 33%). ESI-HRMS: m/z calcd C$_{36}$H$_{62}$N$_4$O$_{11}$** [M+H]$^+$ 727.4488, found 727.4487. Elemental analysis: found C, 58.70; H, 8.70; N, 8.75 calcd for C$_{36}$H$_{62}$N$_4$O$_{11}$, 0.4H$_2$O, 0.7 CH$_3$CN: C, 58.75; H, 8.58; N, 8.61.

The same procedure was used to synthesize (15-{[(7-oxyl-3,11-dioxa-7-azadispiro[5.1.5.3]hexadec-15-yl)carbamoyl][2-(2-methoxyethoxy)ethyl]amino}-[3,11-dioxa-7-azadispiro[5.1.5.3]hexadec-7-yl])oxidanyl 57. ESI-HRMS: m/z calcd C$_{32}$H$_{54}$N$_4$O$_9$** [M+H]$^+$ 639.3964, found 639.3963

Example 4

Synthesis of (15-{[(7-Oxyl-7-azadispiro[5.1.5.3]hexadec-15-yl)carbamoyl]amino}-7-azadispiro[5.1.5.3]hexadec-7-yl)oxidanyl (Compound 53)

4.A. Synthesis of Compound 2

Starting from cyclohexanone and compound 1, General Procedure A of Example 1A was followed to obtain 7-azadispiro[5.1.5.3]hexadecan-15-one 2, mp: 102° C. (lit. 103° C.). $^1$H NMR (300 MHz, CDCl$_3$): 1.35-1.44; (m, 8H), 1.47-1.53; (m, 8H), 1.58-1.68; (m, 4H), 2.29; (s, 4H). $^{13}$C NMR (75 MHz, CDCl$_3$): 22.34, 25.68, 40.78, 52.29, 56.80, 211.47. ESI-MS m/z=236 [M+H]$^+$, 242 [M+Li]$^+$.

4.B. Synthesis of Compound 4

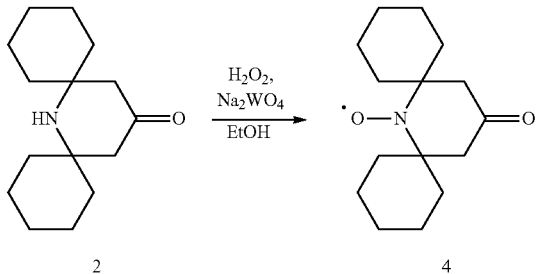

Starting from Compound 2, General procedure B of Example 1.B was followed to obtain (15-oxo-7-azadispiro[5.1.5.3]hexadec-7-yl)oxidanyl 4. ESI-MS m/z=255 [M+H]$^+$, 277 [M+Na]$^+$.

4.C. Synthesis of Compound 4

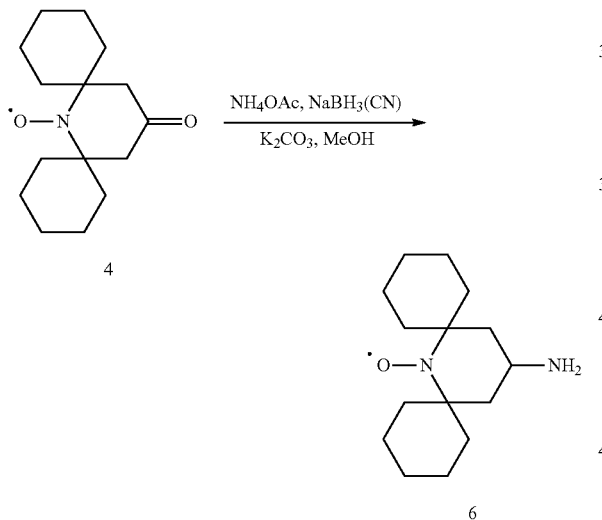

Starting from Compound 4, General procedure C of Example 1.0 was followed to obtain (15-amino-7-azadispiro[5.1.5.3]hexadec-7-yl)oxidanyl 6. ESI-MS m/z=252 [M+H]$^+$.

4.D. Synthesis of Compound 53

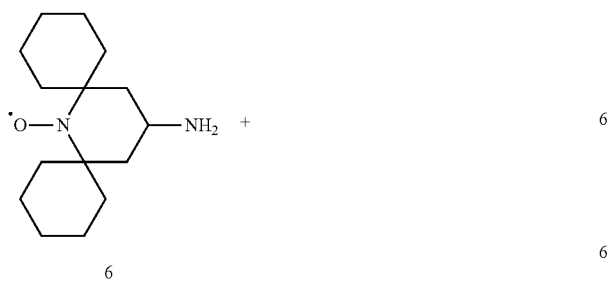

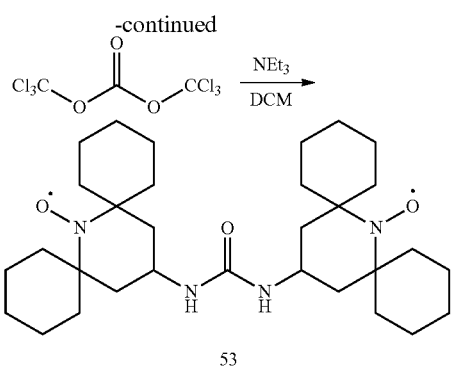

Starting from Compound 6, General Procedure D of Example 1.D was followed to obtain (15-{[(7-oxyl-7-azadispiro[5.1.5.3]hexadec-15-yl)carbamoyl]amino}-7-azadispiro[5.1.5.3]hexadec-7-yl)oxidanyl 53. HRMS-ESI: m/z calcd for C$_{31}$H$_{52}$N$_4$O$_3$ [M+H]$^+$ 529.4112, found 529.4112.

Example 5

Synthesis of (15-{[(7-Hydroxy-7-azadispiro[5.1.5.3]hexadec-15-yl)carbamoyl][2-(2-methoxyethoxy)ethyl]amino}-7-azadispiro[5.1.5.3]hexadec-7-yl)oxidanyl (Compound 54); and Example 6

Synthesis of (15-{[(7-Hydroxy-7-azadispiro[5.1.5.3]hexadec-15-yl)carbamoyl][2-(2-methoxyethoxy)ethyl]amino}-7-azadispiro[5.1.5.3]hexadec-7-yl)oxidanyl (Compound 55)

5A. and 6.A. Syntheses of Compound 8 and Compound 9

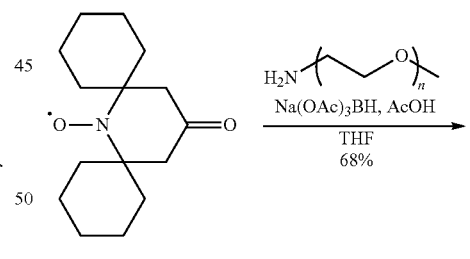

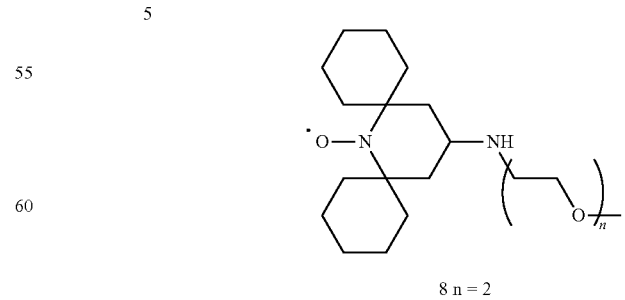

8 n = 2
9 n = 4

Compound 8 (15-{[2-(2-methoxyethoxy)ethyl]amino}-7-azadispiro[5.1.5.3]hexadec-7-yl)oxidanyl was synthesized following General Procedure E of Example 2.A/3.A starting from di(ethylene glycol) methyl ether amine. ESI-MS m/z=354 [M+H]$^+$; 376 [M+Na]$^+$; 392 [M+K]$^+$.

Compound 9 [15-{(2,5,8,11-tetraoxatridecan-13-yl)amino}-7-azadispiro[5.1.5.3]hexadec-7-yl]oxidanyl was synthesized following General Procedure E of Examples 2.A/3.A starting from tetra(ethylene glycol) methyl ether amine. HRMS-ESI: m/z calcd for $C_{24}H_{45}N_2O_5$ [M+H]$^+$ 442.3401, found 442.3394.

5B. and 6.B. Syntheses of Compound 54 and Compound 55

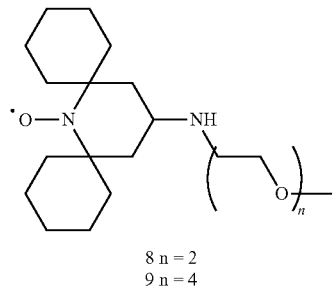

8 n = 2
9 n = 4

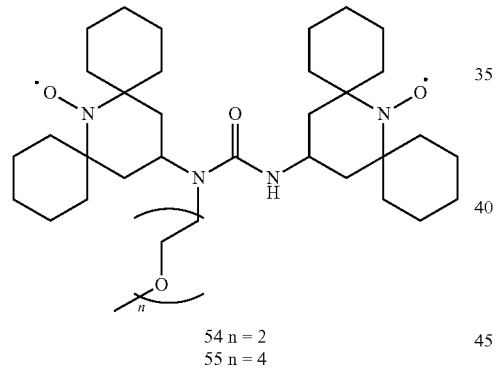

54 n = 2
55 n = 4

Starting from Compounds 5 and 6, General Procedure F of Examples 2.B/3.B. was followed to obtain (15-{[(7-hydroxy-7-azadispiro[5.1.5.3]hexadec-15-yl)carbamoyl][2-(2-methoxyethoxy)ethyl]amino}-7-azadispiro[5.1.5.3]hexadec-7-yl)oxidanyl 54. HRMS-ESI: m/z calcd for $C_{36}H_{62}N_4O_5$ [M+H]$^+$ 631.4793, found 631.4794. Elemental analysis: found C, 68.19; H, 10.11; N, 8.67 calcd $C_{36}H_{62}N_4O$: C, 68.53; H, 9.91; N, 8.88.

Starting from Compounds 9 and 6, General Procedure F of Examples 2.B/3.B. was followed to obtain (15-{[(7-oxyl-7-azadispiro[5.1.5.3]hexadec-15-yl)carbamoyl][2-(2-methoxyethoxy)ethyl]amino}-7-azadispiro[5.1.5.3]hexadec-7-yl)oxidanyl 55. HRMS-ESI: m/z calcd for $C_{40}H_{70}N_4O_7$ [M+H]$^+$ 719.5317, found 719.5316. Anal. Calcd for $C_{40}H_{70}N_4O_7$: C, 66.82; H, 9.81; N, 7.79 found C, 67.01; H, 10.07; N, 8.04.

Example 8

Synthesis of (4-{[2-(2-Methoxyethoxy)ethyl][(1-oxyl-2,2,6,6-tetramethylpiperidin-4-yl)carbamoyl]amino}-2,2,6,6-tetramethylpiperidin-1-yl)oxidanyl (Compound 51); and

Example 9

Synthesis of (4-{(2,5,8,11-Tetraoxatridecan-13-yl)[(1-oxyl-2,2,6,6-tetramethylpiperidin-4-yl)carbamoyl]amino}-2,2,6,6-tetramethylpiperidin-1-yl)oxidanyl (Compound 52)

8.A. and 9.A. Syntheses of Compound 14 and Compound 15

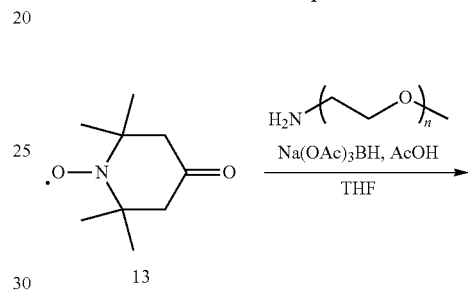

13

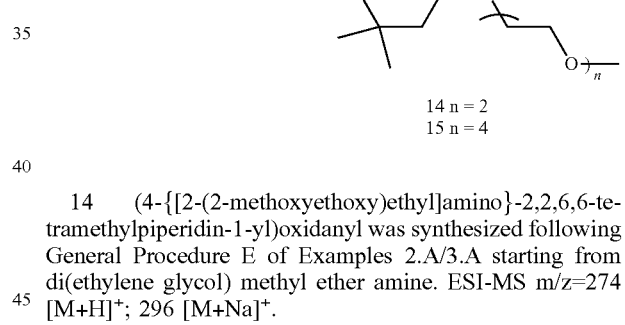

14 n = 2
15 n = 4

14 (4-{[2-(2-methoxyethoxy)ethyl]amino}-2,2,6,6-tetramethylpiperidin-1-yl)oxidanyl was synthesized following General Procedure E of Examples 2.A/3.A starting from di(ethylene glycol) methyl ether amine. ESI-MS m/z=274 [M+H]$^+$; 296 [M+Na]$^+$.

15 (4-{(2,5,8,11-tetraoxatridecan-13-yl)amino}-2,2,6,6-tetramethylpiperidin-1-yl)oxidanyl was synthesized following General Procedure E of Examples 2.A/3.A starting from tetra(ethylene glycol) methyl ether amine. HRMS-ESI: m/z calcd for $C_{18}H_{37}N_2O_5$ [M+H]$^+$ 362.2775, found 362.2778

8.B. and 9.B. Syntheses of Compound 51 and Compound 52

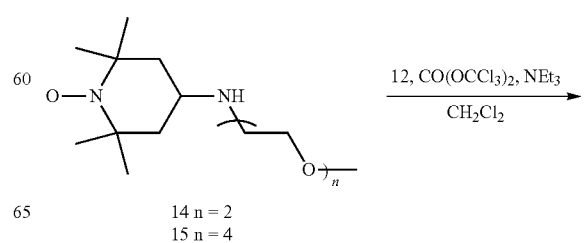

14 n = 2
15 n = 4

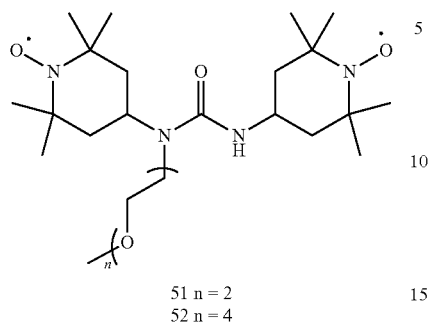

51 n = 2
52 n = 4

(4-{[2-(2-Methoxyethoxy)ethyl][(1-oxyl-2,2,6,6-tetramethylpiperidin-4-yl)carbamoyl]amino}-2,2,6,6-tetramethylpiperidin-1-yl)oxidanyl 51 was synthesized following General Procedure F of Examples 2.B/3.B starting from Compounds 14 and 12. HRMS-ESI: m/z calcd for $C_{24}H_{46}N_4O_5$ [M+H]$^+$ 471.3540, found 471.3538. Anal. Calcd for C24H46N4O5: C, 61.25; H, 9.85; N, 11.90. Found C, 61.17; H, 10.06; N, 11.65.

(4-{(2,5,8,11-Tetraoxatridecan-13-yl)[(1-oxyl-2,2,6,6-tetramethylpiperidin-4-yl)carbamoyl]amino}-2,2,6,6-tetramethylpiperidin-1-yl)oxidanyl 52 was synthesized following General Procedure F of Examples 2.B/3.B starting from Compounds 15 and 12. HRMS-ESI: m/z calcd for $C_{28}H_{54}N_4O_7$ [M+H]$^+$ 559.4065, found 559.4063.

Example 10

Synthesis of 4-{(5-Carboxypentyl)[(1-oxyl-2,2,6,6-tetramethylpiperidin-4-yl)carbamoyl]amino}-2,2,6,6-tetramethylpiperidin-1-yl)oxidanyl (Compound 59)

10.A. Synthesis of Compound 17

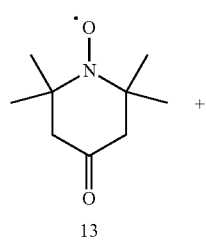

13

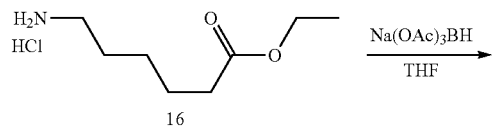

16

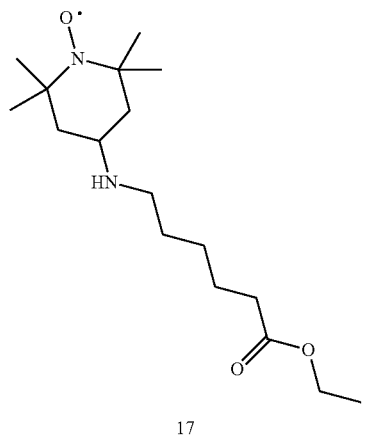

17

(4-{(6-Ethoxy-6-oxohexyl)amino}-2,2,6,6-tetramethylpiperidin-1-yl)oxidanyl 17 was synthesized following General Procedure E of Examples 2.A/3.A starting from ethyl 6-aminohexanoate hydrochloride and Compound 13. ESI-MS m/z=314 [M+H]$^+$, 320 [M+Li]$^+$.

10.B. Synthesis of Compound 18

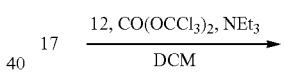

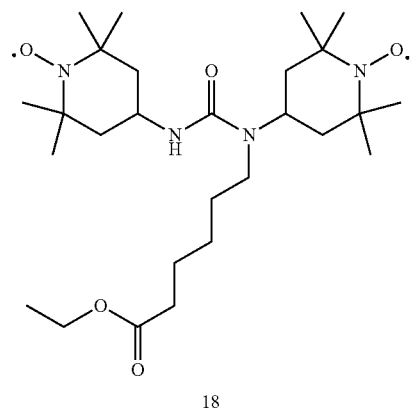

18

(4-{(6-Ethoxy-6-oxohexyl)[(1-oxyl-2,2,6,6-tetramethylpiperidin-4-yl)carbamoyl]amino}-2,2,6,6-tetramethylpiperidin-1-yl)oxidanyl 18 was synthesized following General Procedure F of Examples 2.B/3.B starting from Compounds 17 and 12. ESI-MS m/z=511 [M+H]$^+$, 517 [M+Li]$^+$

10.C. Synthesis of Compound 18

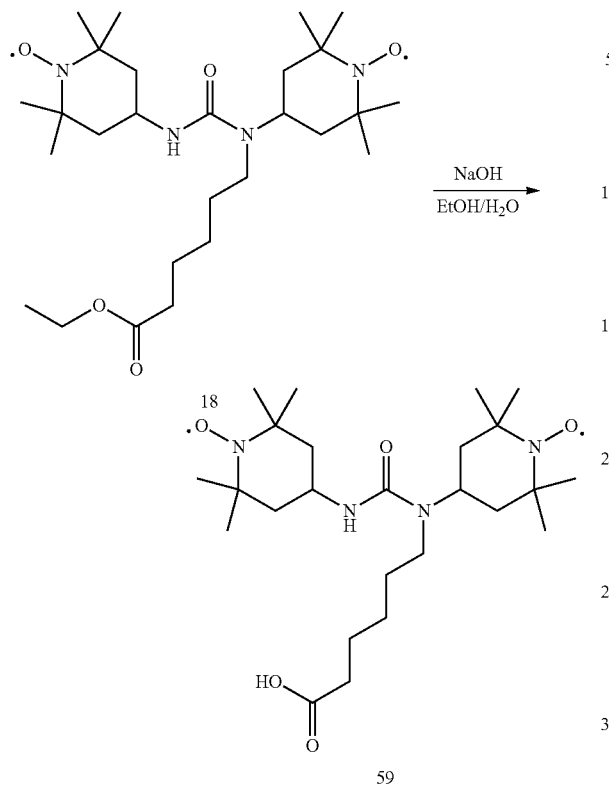

A solution of 18 (820 mg, 1.6 mmol) and NaOH (320 mg, 8.0 mmol) in a 8:2 mixture EtOH:H$_2$O (10 ml) was stirred at 70° C. for 12 h. EtOH was removed under vacuum. Using 1M HCl aqueous solution, pH of the remaining water phase was adjusted at 3. The aqueous phase was then extracted with DCM. The residue was purified using flash chromatography to give (4-{(5-carboxypentyl)[(1-oxyl-2,2,6,6-tetramethylpiperidin-4-yl)carbamoyl]amino}-2,2,6,6-tetramethylpiperidin-1-yl)oxidanyl 59 as a red solid (505 mg, 1.05 mmol, 65%). HRMS-ESI: m/z calcd for C$_{25}$H$_{46}$N$_4$O$_5$* [M+H]$^+$ 483.3541, found 483.3541. Elemental analysis: found C, 61.24; H, 9.70; N, 11.31 calcd for C$_{25}$H$_{46}$N$_4$O$_5$, 0.4H$_2$O: C, 61.30; H, 9.63; N, 11.44.

Example 11

Synthesis of (4-{[2-(2-Methoxyethoxy)ethyl][(1-oxyl-2,2,6,6-tetramethylpiperidin-4-yl)carbamoyl]amino}-2,2,6,6-tetramethylpiperidin-1-yl)oxidanyl (Compound 60)

11.A. Synthesis of Compound 19

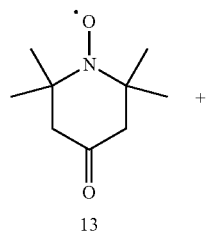

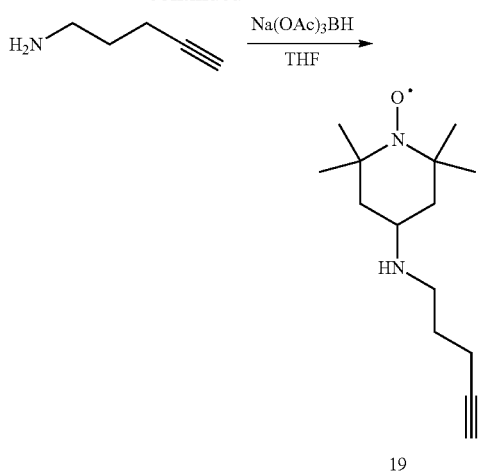

[2,2,6,6-Tetramethyl-4-(pent-4-yn-1-ylamino)piperidin-1-yl]oxidanyl 19 was synthesized following General Procedure E of Examples 2.A/3.A starting from pent-4-yn-1-amine and Compound 13. HRMS-ESI: m/z calcd for C$_{14}$H$_{25}$N$_2$O* [M+H]$^+$ 238.2039, found 238.2041

11.B. Synthesis of Compound 60

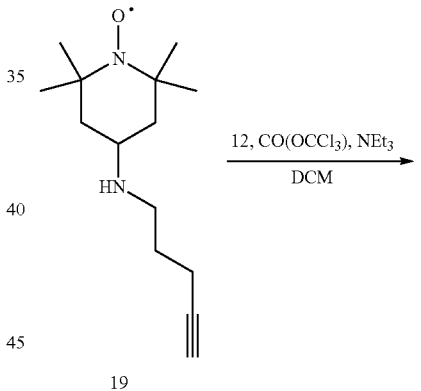

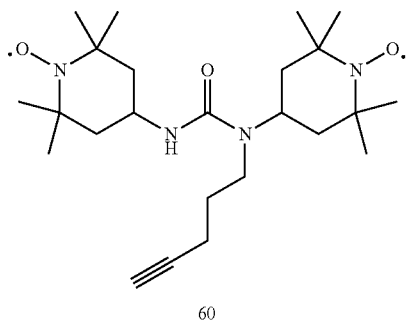

(4-{(Pent-4-yn-1-yl)[(1-oxyl-2,2,6,6-tetramethylpiperidin-4-yl)carbamoyl]amino}-2,2,6,6-tetramethylpiperidin-1-yl)oxidanyl 60 was synthesized following General procedure F of Example 2.B/3.B starting form Compound 19. HRMS-ESI: m/z calcd for C$_{24}$H$_{42}$N$_4$O$_3$** [M+H]$^+$ 435.3330, found 435.3333

Example 12

Synthesis of (4-{3-[1-(PEG)-1H-1,2,3-Triazol-4-yl]propyl}[(1-oxyl-2,2,6,6-tetramethylpiperidin-4-yl)carbamoyl]amino}-2,2,6,6-tetramethylpiperidin-1-yl)oxidanyl (Compound 61)

Example 13

Synthesis of 1,3-Bis(1-oxyl-2,2,6,6-tetramethylpiperidin-4-yl)imidazolidin-2-one (Compound 62); and

Example 14

Synthesis of 1,3-Bis(1-oxyl-2,2,6,6-tetramethylpiperidin-4-yl)tetrahydropyrimidin-2(1H)-one (Compound 63)

13.A. and 14.A. Syntheses of Compound 23 and Compound 24

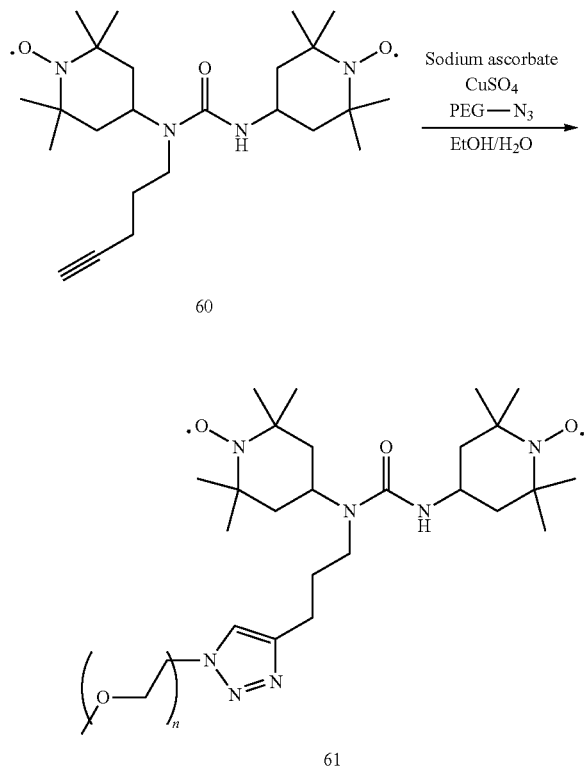

Following General Procedure E of Examples 2.A/3.A starting from Compound 20, 4,4'-(ethane-1,2-diyldiimino)bis(2,2,6,6-tetramethylpiperidin-1-oxidanyl) 22 was obtained. HRMS-ESI: m/z calcd for $C_{20}H_{40}N_4O_2$**[M+H]$^+$ 369.3224, found 369.3223

Following General Procedure E of Examples 2.A/3.A starting from Compound 21, 4,4'-(propane-1,3-diyldiimino)bis(2,2,6,6-tetramethylpiperidin-1-oxidanyl) 23 was obtained. HRMS-ESI: m/z calcd for $C_{21}H_{42}N_4O_2$**[M+H]$^+$ 383.3381, found 383.3386

13.B. and 14.B. Syntheses of Compound 62 and Compound 63

A solution of 60 (50 mg, 0.12 mmol) and PEG-N$_3$ M$_n$=500 (62 mg, 0.12 mmol) in EtOH (3 mL) was diluted with water (2 mL). Sodium ascorbate (1M solution in water, 24 μL, 0.024 mmol, 20 mol %) and copper(II) sulfate pentahydrate (1 M solution in water, 12 μL, 0.012 mmol, 10 mol %) were added. After being stirred at room temperature for 6 h, the solution was concentrated in vacuo. The resulting residue was purified by column chromatography to afford crude compound 61 as a red oil (15 mg) which was further purified on prep-HPLC to afford 11 mg of pure (4-{3-[1-(PEG)-1H-1,2,3-triazol-4-yl]propyl}[(1-oxyl-2,2,6,6-tetramethylpiperidin-4-yl)carbamoyl]amino}-2,2,6,6-tetramethylpiperidin-1-yl)oxidanyl 61 as an oil (0.01 mmol, 10%). HRMS-ESI: m/z calcd for $C_{25}H_{45}N_4O_3$$(C_2H_4O)_7$[M+H]$^+$ 800.5492, found 800.5495; m/z calcd for $C_{25}H_{45}N_4O_3$$(C_2H_4O)_8$[M+H]$^+$ 844.5754, found 544.5758; m/z calcd for $C_{25}H_{45}N_4O_3$$(C_2H_4O)_9$[M+H]$^+$ 888.6016, found 888.6024; m/z calcd for $C_{25}H_{45}N_4O_3$$(C_2H_4O)_{10}$[M+H]$^+$ 932.6278, found 932.6280

-continued

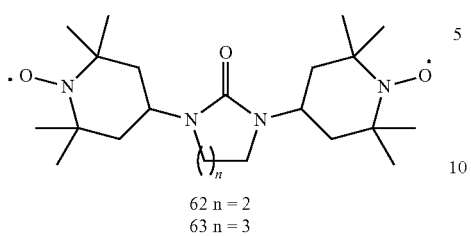

62 n = 2
63 n = 3

To a 0.01 M solution of 22 (100 mg, 0.27 mmol) in DCM was added a solution of triphosgene (28 mg, 0.09 mmol) in DCM (1 ml) and the solution was stirred at rt overnight.

The reaction mixture was washed with sat. aq. NaHCO$_3$, dried over Na$_2$SO$_4$ and the solvent removed under reduce pressure. The residue was purified by column chromatography (SiO$_2$, DCM:MeOH, 97:3) to give 1,3-bis(1-oxyl-2,2,6,6-tetramethylpiperidin-4-yl)imidazolidin-2-one 62 as a red solid (50 mg, 0.13 mmol, 47%). HRMS-ESI: m/z calcd for C$_{21}$H$_{38}$N$_4$O$_3$** [M+H]$^+$ 395.3017, found 395.3013.

1,3-Bis(1-oxyl-2,2,6,6-tetramethylpiperidin-4-yl)tetrahydropyrimidin-2(1H)-one 63 was synthesized in an analogous manner starting from Compound 23. HRMS-ESI: m/z calcd for C$_{22}$H$_{40}$N$_4$O$_3$** [M+H]$^+$ 409.3173, found 409.3178

Example 15

Synthesis of (3-{[(1-Oxyl-2,2,5,5-tetramethylpyrrolidin-3-yl) carbamoyl]amino}[2,2,5,5-tetramethylpyrrolidin-3-yl])oxidanyl (Compound 64)

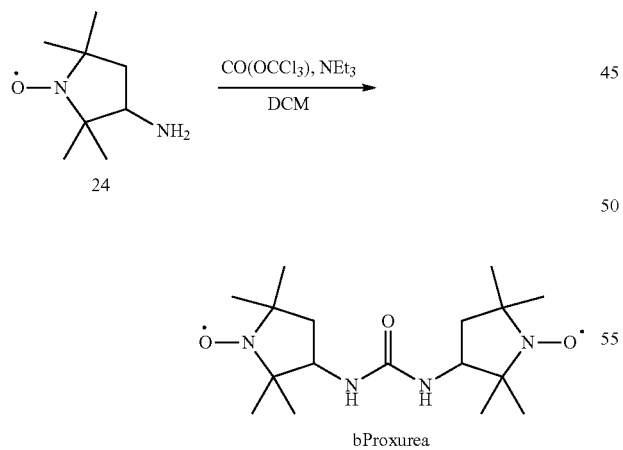

bProxurea (3-{[(1-Oxyl-2,2,5,5-tetramethylpyrrolidin-3-yl) carbamoyl]amino}-[2,2,5,5-tetramethylpyrrolidin-3-yl])oxidanyl 64 was synthesized following General Procedure D of Example 1.D. starting from Compound 24. HRMS-ESI: m/z calcd for C$_{17}$H$_{32}$N$_4$O$_3$** [M+H]+ 341.2547. found 341.2547.

Example 16

Synthesis of (4-{[(1-Oxyl-2,2,6,6-tetramethylpiperidin-4-yl)carbonyl]amino}-2,2,6,6-tetramethylpiperidin-1-yl)oxidanyl (Compound 65)

16.A. Synthesis of Compound 25

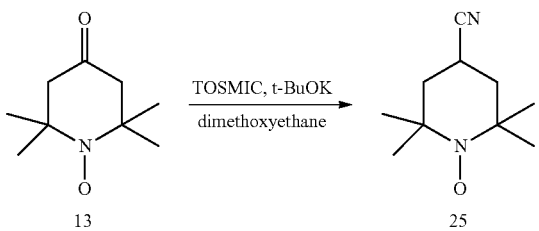

To a stirred solution of (2,2,6,6-tetramethyl-4-oxopiperidin-1-yl)oxidanyl (1.00 g, 5.88 mmol) and tosylmethyl isocyanide (1.30 g, 6.66 mmol) in dimethoxyethane (20 mL) was added slowly a solution of potassium tert-butoxide (1.30 g, 11.60 mmol) dissolved in a mixture of dimethoxyethane (10 mL) and tert-butyl alcohol (10 mL). The mixture was stirred for 3 h at room temperature. At the end of reaction, 100 ml of water was added and the mixture was extracted with diethylether (80 ml), dried over Na$_2$SO$_4$ and concentrated under reduced pressure to give (4-cyano-2,2,6,6-tetramethylpiperidin-1-yl)oxidanyl 25 (0.95 g, 89%) as a red powder. ESI-MS: [M+H]$^+$=182; [M+Na]$^+$=204.

16.B. Synthesis of Compound 26

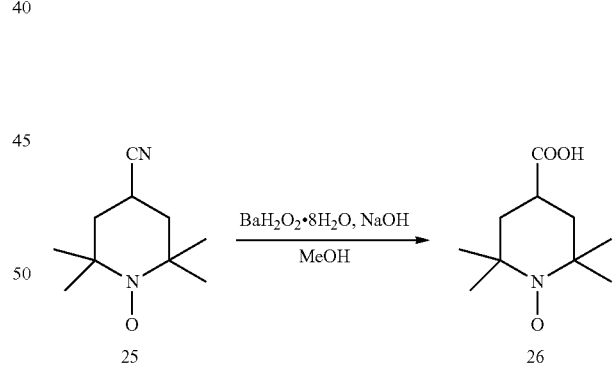

To a solution of 25 (0.90 g, 4.97 mmol) in methanol (20 mL) was added a solution of Ba(OH)$_2$.8H$_2$O (3.00 g, 9.52 mmol) in 100 mL of water. The mixture was refluxed during 6 h. At the end of time, the mixture was cooled, and extracted with chloroform (2×200 mL). Then, the aqueous solution was acidified with 5% hydrochloric acid, and extracted with chloroform (3×200 mL). The chloroform extracts were recombined, dried over Na$_2$SO$_4$ and concentrated under reduced pressure to give (4-carboxy-2,2,6,6-tetramethylpiperidin-1-yl)oxidanyl 26 (0.82 g, 82%) as a red powder. mp: 171° C.; HRMS-ESI: calcd for C$_{10}$H$_{18}$NO$_3$ ([M+H]$^+$) 201.1359. found 201.1359.

16.C. Synthesis of Compound 65

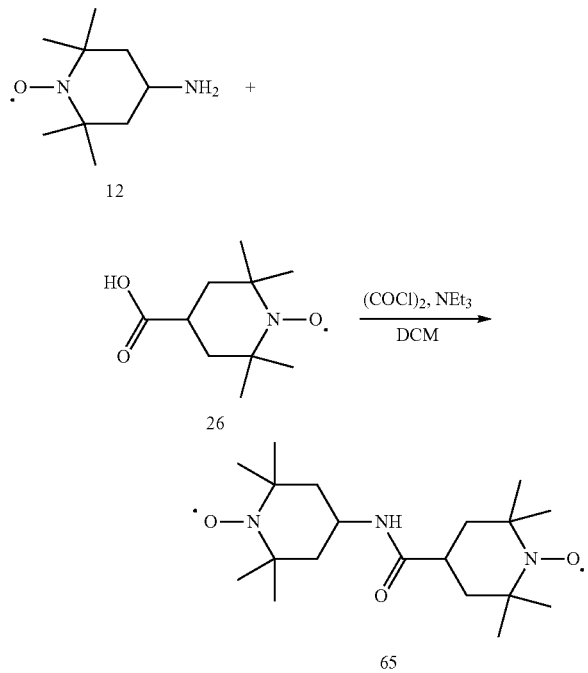

To a solution of 26 (50 mg, 0.25 mmol) under Argon atmosphere in DCM was added oxalyl chloride (26 µl, 0.3 mmol). The solution was stirred at rt for 3 h. Then the excess of oxalyl chloride and DCM were removed in vacuo. To a solution of 12 (43 mg, 0.25 mmol) in DCM was added the solution of the acid chloride in DCM dropwise and the resulting solution was stirred at rt for 2 h. It was then washed with sat. aq. NaHCO$_3$ and the solvent was removed under reduced pressure. The residue was purified using flash chromatography to give 40 mg of red solid (4-{[(1-oxyl-2,2,6,6-tetramethylpiperidin-4-yl)carbonyl]amino}-2,2,6,6-tetramethylpiperidin-1-yl)oxidanyl 65 (0.11 mmol, 45%). HRMS-ESI: calcd for C$_{19}$H$_{35}$N$_3$O$_3$[M+H]$^+$ 354.2754, found 354.2748.

Example 17

Synthesis of (4-{[(1-Oxyl-2,2,6,6-tetramethylpiperidin-4-yl)carbonyl]amino}-2,2,6,6-tetramethylpiperidin-1-yl)oxidanyl (Compound 66) (General Procedure G)

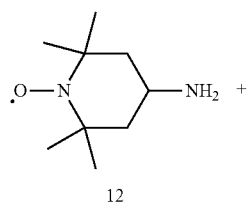

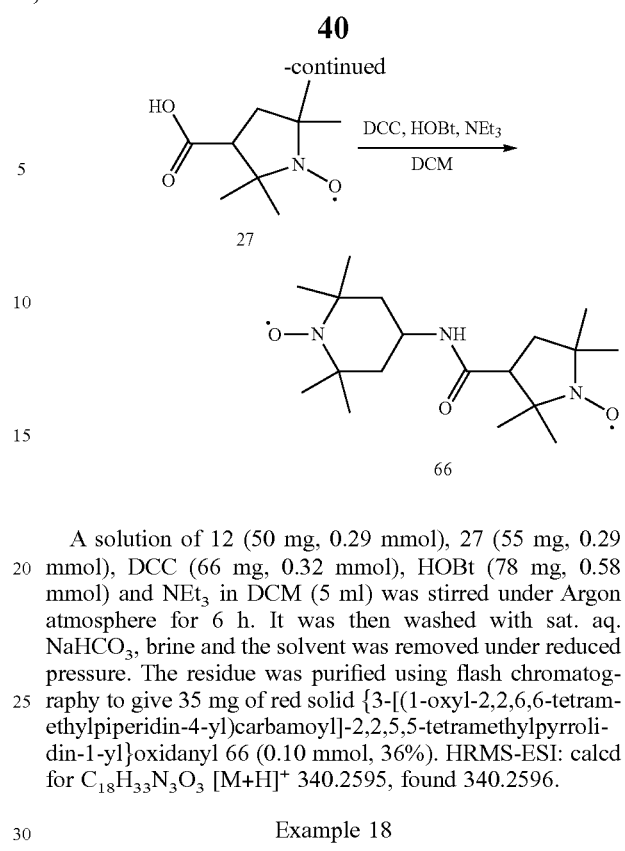

A solution of 12 (50 mg, 0.29 mmol), 27 (55 mg, 0.29 mmol), DCC (66 mg, 0.32 mmol), HOBt (78 mg, 0.58 mmol) and NEt$_3$ in DCM (5 ml) was stirred under Argon atmosphere for 6 h. It was then washed with sat. aq. NaHCO$_3$, brine and the solvent was removed under reduced pressure. The residue was purified using flash chromatography to give 35 mg of red solid {3-[(1-oxyl-2,2,6,6-tetramethylpiperidin-4-yl)carbamoyl]-2,2,5,5-tetramethylpyrrolidin-1-yl}oxidanyl 66 (0.10 mmol, 36%). HRMS-ESI: calcd for C$_{18}$H$_{33}$N$_3$O$_3$ [M+H]$^+$ 340.2595, found 340.2596.

Example 18

Synthesis of (3-{[(1-oxyl-2,2,6,6-tetramethylpiperidin-4-yl)carbonyl]amino}-2,2,5,5-tetramethylpyrrolidin-1-yl)oxidanyl (Compound 67)

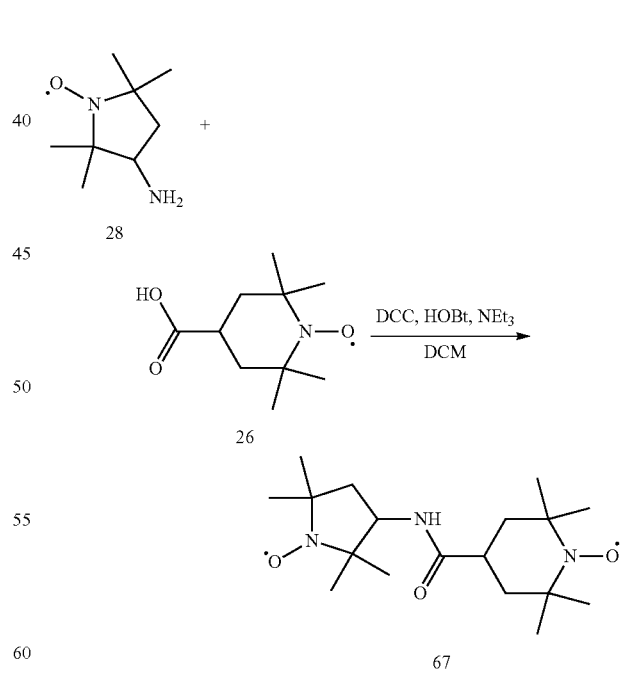

(3-{[(1-Oxyl-2,2,6,6-tetramethylpiperidin-4-yl)carbonyl]amino}-2,2,5,5-tetramethylpyrrolidin-1-yl)oxidanyl 67 was synthesized following General Procedure G. of Example 17 starting from Compounds 28 and 26. HRMS-ESI: calcd for C$_{18}$H$_{33}$N$_3$O$_3$ [M+H]$^+$ 340.2595, found 340.2594.

Example 19

Synthesis of (4-{[(1-Oxyl-2,2,6,6-tetramethylpiperidin-4-yl)sulfamoyl]amino}-2,2,6,6-tetramethylpiperidin-1-yl)oxidanyl (Compound 68)

19.A. Synthesis of Compound 30

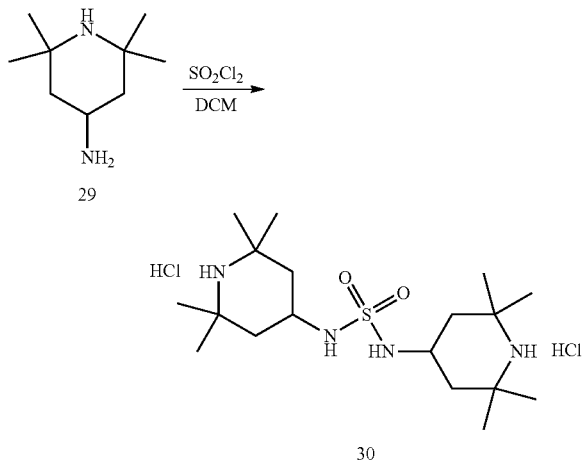

Under an argon atmosphere, to a solution of 29 (312 mg, 2 mmol) in DCM was added a solution of sulfuryl chloride (81 µl, 1 mmol) in DCM (1 ml) and the solution was stirred for 2 h. The precipitate of 30 was filtrated and used without further purification.

19.B. Synthesis of Compound 68

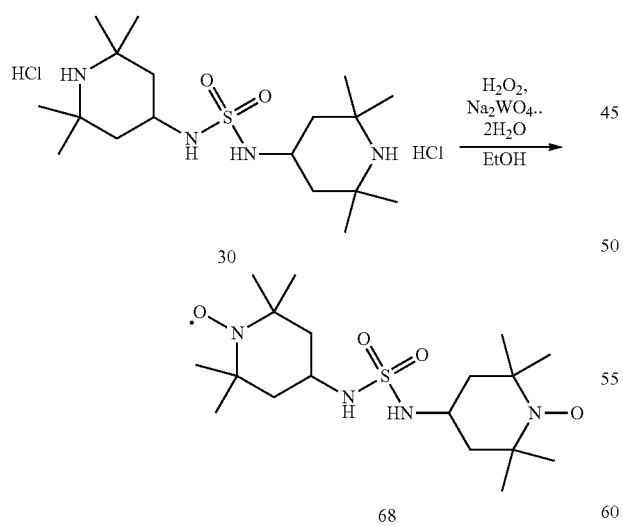

Following General procedure B of Example 1.B starting from Compound 30, (4-{[(1-oxyl-2,2,6,6-tetramethylpiperidin-4-yl)sulfamoyl]amino}-2,2,6,6-tetramethylpiperidin-1-yl)oxidanyl 68 was synthesized. HRMS-ESI: calcd for $C_{18}H_{36}N_4O_4S$ [M+H]$^+$ 405.2530, found 405.2530.

Example 20

Synthesis of 5-Hydroxy-1,3-bis(7-oxyl-3,11-dioxa-7-azadispiro[5.1.5.3]-hexadec-15-yl)tetrahydropyrimidin-2(1H)-one (Compound 69) and 1,3-Bis(7-oxyl-3,11-dioxa-7-azadispiro[5.1.5.3]hexadec-15-yl)-5-(2,5,8,11-tetraoxatridecan-13-yloxy)tetrahydropyrimidin-2(1H)-one (Compound 70)

20.A. Synthesis of Compound 32

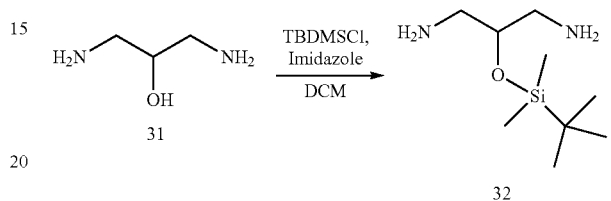

Over a solution of 31 (0.25 g, 2.77 mmol) in $CH_2Cl_2$ (20 mL) at 0° C. was added imidazole (566 mg, 8.33 mmol), DMAP (67 mg, 0.27 mmol) and tert-butyldimethylsilyl chloride (666 mg, 5.55 mmol). The solution was stirred for 5 h at room temperature, after this time the solvent was removed by distillation at reduced pressure obtaining a crude that was purified by flash chromatography (10-30% EtOH/$CH_2Cl_2$) affording 32 as an oil (0.5 g, 85%). $^1$H NMR (400 MHz, CHLOROFORM-d) δppm 0.10; (s, 6H); 0.87-0.95; (m, 9H); 2.76; (dd, J=5.14, 3.89 Hz, 3H); 3.61; (quin, J=5.21 Hz, 1H); $^{13}$C NMR (75 MHz, CHLOROFORM-d) δppm: −4.49; 18.09: 25.84; 45.67; 75.10.

20.B. Synthesis of Compound 33

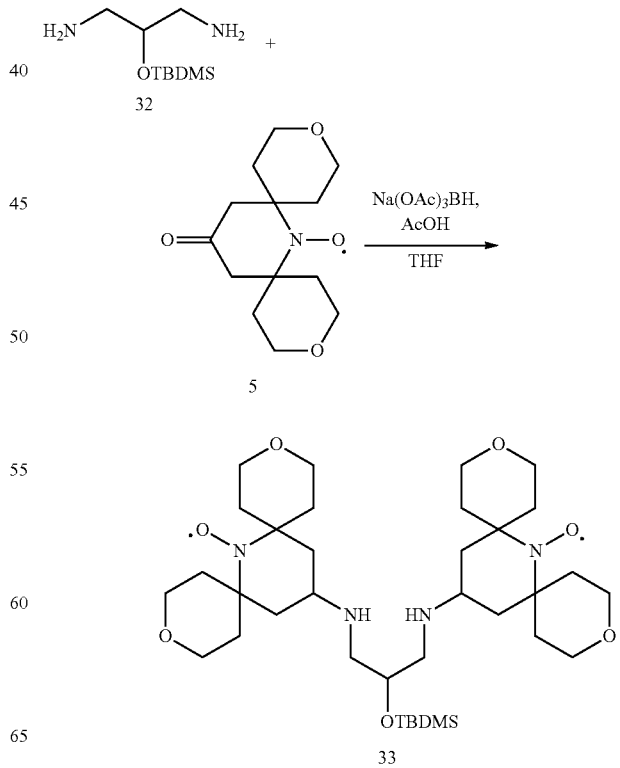

To a solution of ketone 5 (750 mg, 2.95 mmol), diamine 32 (251 mg, 1.23 mmol) in dry THF (10 ml) was added AcOH to adjust the pH at 6-7 and the solution was stirred at rt for 2 h. Then, Na(OAc)$_3$BH (630 mg, 3.69 mmol) was added portion wise and the reaction was stirred at rt for 16 h. After this time, the mixture was concentrated under reduced pressure. The residue was solubilized in CH$_2$Cl$_2$, washed with a saturated aqueous solution of NaHCO$_3$, dried on Na$_2$SO$_4$, concentrated under reduced pressure and the crude product was purified by SiO$_2$ column chromatography with CH$_2$Cl$_2$/MeOH (9/1) to give the desired compound 33 (425 mg, 0.62 mmol, 51%). HRMS-ESI: m/z calcd for C$_{35}$H$_{65}$N$_4$O$_7$Si [M+H]$^+$ 681.4617, found 681.4614.

20.C. Synthesis of Compound 34

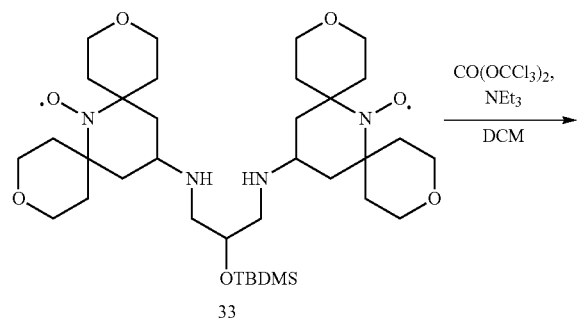

33

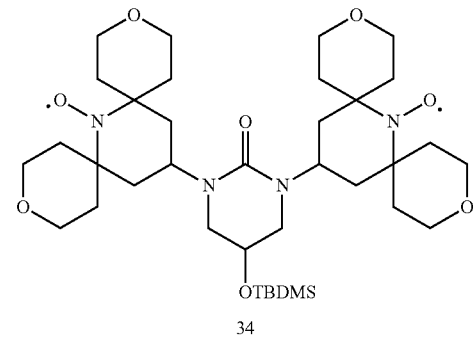

34

To a 0.01 M solution of 33 (425 mg, 0.62 mmol) and NEt$_3$ (0.2 ml, 1.36 mmol) in DCM was added under Ar at 0° C. a solution of triphosgene (61 mg, 0.20 mmol) in DCM (1 ml) and the solution was stirred at it overnight. The reaction mixture was washed with sat. aq. NaHCO$_3$, dried over Na$_2$SO$_4$ and the solvent removed under reduced pressure. The residue was purified by column chromatography (SiO$_2$, DCM:MeOH, 97:3) to give 34 as a red solid (310 mg, 0.44 mmol, 71%). HRMS-ESI: m/z calcd for C$_{36}$H$_{63}$N$_4$O$_8$Si [M+H]$^+$ 707.4410, found 707.4410.

20.D. Synthesis of Compound 69

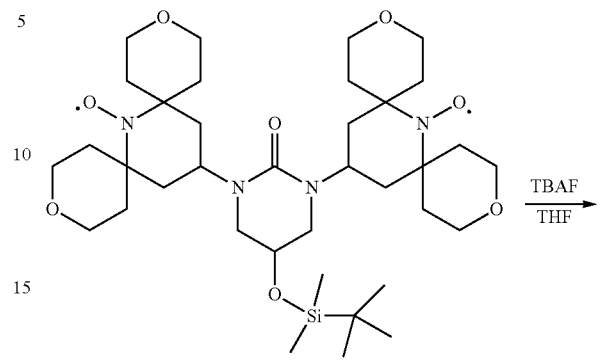

A 1 M solution of TBAF (0.47 ml, 0.47 mmol) was added to a stirred solution of 34 (310 mg, 0.44 mmol) in THF (5 ml). The solution was stirred at it for 2 h (until completion, followed by TLC), brine was added and it was extracted with AcOEt. The organic phase was dried over Na$_2$SO$_4$ and the solvent removed under reduced pressure. The residue was purified by column chromatography (SiO$_2$, DCM:MeOH, 95:5) to give 5-hydroxy-1,3-bis(7-oxyl-3,11-dioxa-7-azadispiro[5.1.5.3]hexadec-15-yl)tetrahydropyrimidin-2 (1H)-one 69 as a red solid (250 mg, 0.42 mmol, 95%). HRMS-ESI: m/z calcd for C$_{30}$H$_{49}$N$_4$O$_8$ [M+H]$^+$ 593.3545, found 593.3550.

20.E. Synthesis of Compound 70

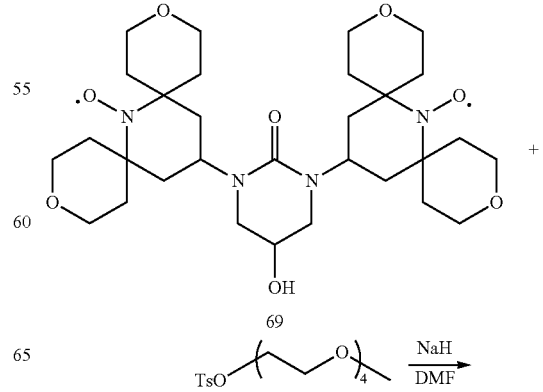

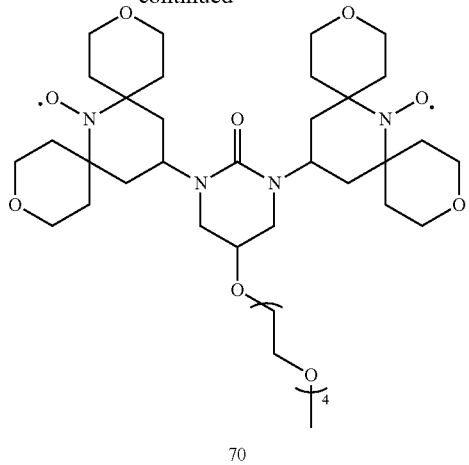

70

NaH (60%, 30 mg, 0.18 mmol) was added to a solution of 69 (75 mg, 0.12 mmol) in DMF and stirred at it for 3 h. Then a solution of tosylated PEG (66 mg, 0.18 mmol) was added and the reaction mixture was stirred at rt for 5 h. Brine was added and the mixture was extracted with DCM, dried over Na$_2$SO$_4$ and the solvent removed under reduced pressure. The residue was purified by column chromatography (SiO$_2$, DCM:EtOH, 95:5) to give 1,3-bis(7-oxyl-3,11-dioxa-7-azadispiro[5.1.5.3]hexadec-15-yl)-5-(2,5,8,11-tetraoxatridecan-13-yloxy)tetrahydropyrimidin-2(1H)-one 70 as a red solid (25 mg, 0.03 mmol, 27%). HRMS-ESI: m/z calcd for C$_{39}$H$_{70}$N$_5$O$_{12}$ [M+NH$_4$]$^+$ 800.5016, found 800.5015.

Example 20

Synthesis of (15-{[(7-Oxyl-3,11-dioxa-7-azadispiro[5.1.5.3]hexadec-15-yl)carbamoyl][2-(2-hydroxyethoxy)ethyl]amino}-3,11-dioxa-7-azadispiro[5.1.5.3]hexadec-7-yl)oxidanyl (Compound 71)

20.A. Synthesis of Compound 36

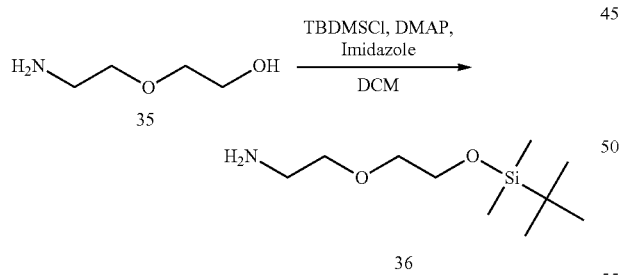

Over a solution of 2-(2-aminoethoxy)ethanol (35) (5.0 ml, 50.3 mmol) in CH$_2$Cl$_2$ (30 ml) at 0° C. was added imidazole (10.3 g, 151 mmol), DMAP (0.6 g, 5 mmol) and tert-butyldimethylsilyl chloride (8.3 g, 55 mmol). The solution was stirred for 5 h at room temperature, then washed with brine and the solvent was removed under reduced pressure to obtain 36 as an oil (7.5 g, 68%). $^1$H NMR (300 MHz, CHLOROFORM-d) δppm: −0.03 (s, 6H); 0.80; (s, 9H); 2.87; (t, J=5.18 Hz, 2H); 3.44; (m, J=5.23 Hz, 2H); 3.52; (t, J=5.18 Hz, 2H); 3.66; (t, J=4.86 Hz, 2H). $^{13}$C NMR (75 MHz, CHLOROFORM-d) δppm −5.49 (s, 2 CH$_3$); 18.12; (s, C); 25.69; (s, 3 CH$_3$); 40.53; (s, CH$_2$); 62.46; (s, CH$_2$); 70.45; (s, CH$_2$); 72.22; (s, CH$_2$).

20.B. Synthesis of Compound 37

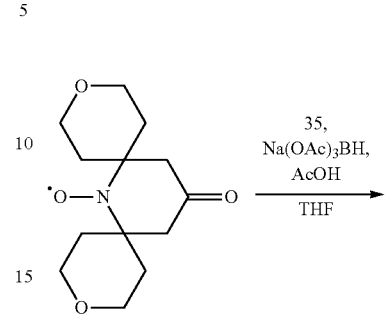

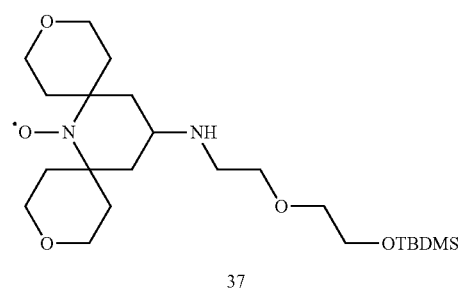

Compound 37 was synthesized following General Procedure E of Example 2.A/3.A starting from Compounds 5 and 35. HRMS-ESI: m/z calcd C$_{23}$H$_{46}$N$_2$O$_5$Si$^{*+}$ [M+H]$^+$ 458.3171, found 458.3166.

20.C. Synthesis of Compound 38

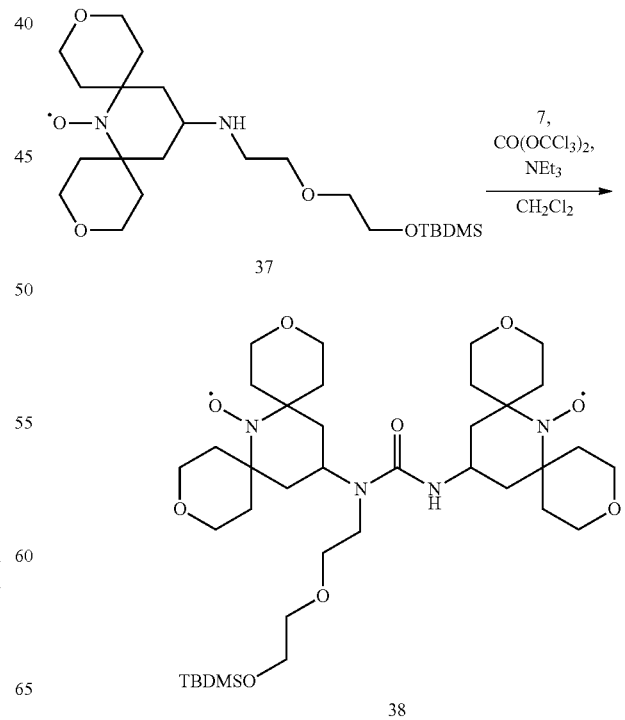

Compound 38 was synthesized following General procedure F of Example 2.B/3.B starting form Compound 37. HRMS-ESI: m/z calcd $C_{37}H_{67}N_4O_9Si^{**+}$ [M+H]$^+$ 739.4672, found 739.4669.

20.D. Synthesis of Compound 71

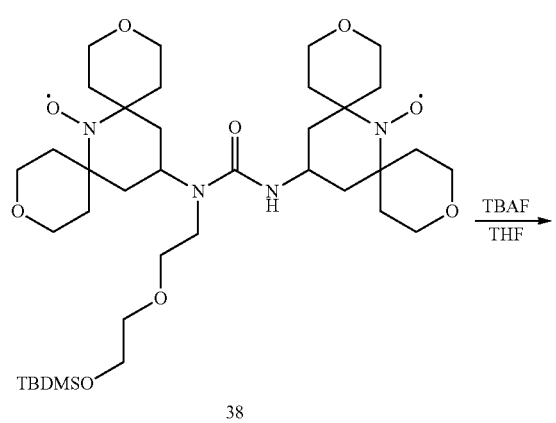

38

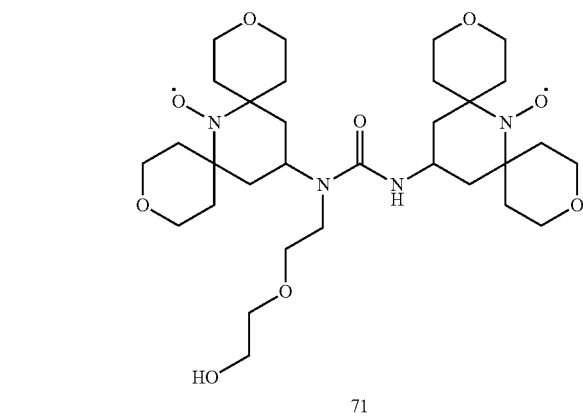

71

A 1 M solution of tetrabutyl ammonium chloride (TBAF) (1.8 ml, 1.8 mmol) was added to a stirred solution of 38 (1.33 g, 1.8 mmol) in THF (30 ml). The solution was stirred at rt for 2 h (until completion, followed by TLC), brine was added and it was extracted with AcOEt. The organic phase was dried over $Na_2SO_4$ and the solvent removed under reduced pressure. The residue was purified by column chromatography (SiO$_2$, DCM:MeOH, 96:4) to give (15-{[(7-oxyl-3,11-dioxa-7-azadispiro[5.1.5.3]hexadec-15-yl)carbamoyl][2-(2-hydroxyethoxy)ethyl]amino}-[3,11-dioxa-7-azadispiro[5.1.5.3]hexadec-7-yl])oxidanyl 71 as a red solid (1.07 g, 1.71 mmol, 95%). HRMS-ESI: m/z calcd for $C_{31}H_{53}N_4O_9$ [M+H]$^+$ 625.3807, found 625.3799.

Example 21

Synthesis of α-{(7-Oxyl-3,11-dioxa-7-azadispiro[5.1.5.3]hexadec-15-yl)[(7-oxyl-3,11-dioxa-7-azadispiro[5.1.5.3]hexadec-15-yl)carbamoyl]amino}ω-methylpoly(ethane-1,2-diyloxy) (Compound 72)

21.A. Syntheses of Compound 39

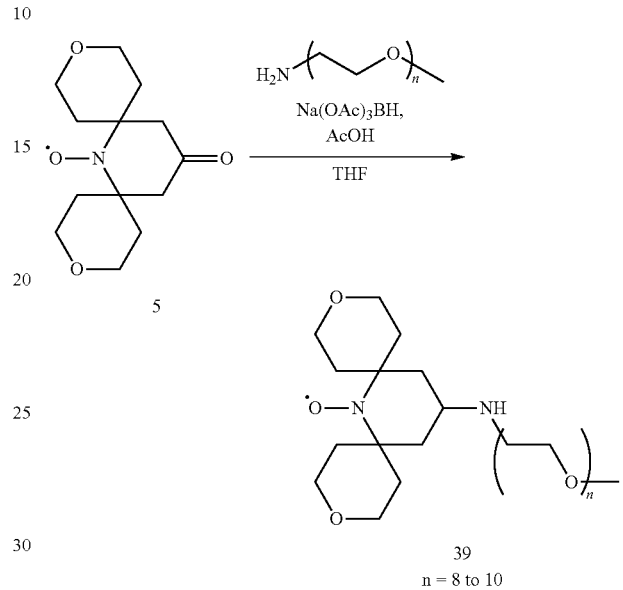

39
n = 8 to 10

Compound 39 was synthesized following General procedure E of Example 2.A/3.A starting from poly((ethylene glycol) methyl ether ($M_n$=500 g·mol$^{-1}$).

21.B. Syntheses of Compound 72

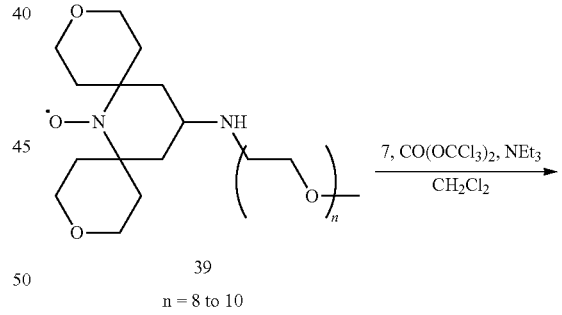

39
n = 8 to 10

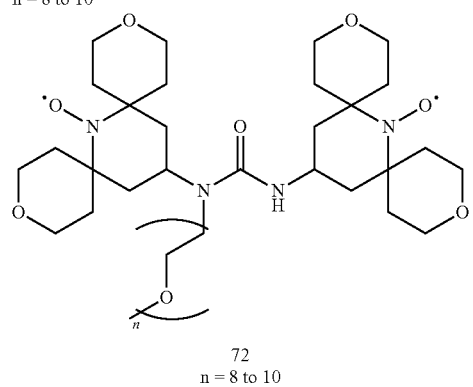

72
n = 8 to 10

α-{(7-Oxyl-3,11-dioxa-7-azadispiro[5.1.5.3]hexadec-15-yl)[(7-oxyl-3,11-dioxa-7-azadispiro[5.1.5.3]hexadec-15-yl)carbamoyl]amino}ω-methylpoly(ethane-1,2-diyloxy) 72 was synthesized following General Procedure F of Example 2.B/3.B starting from Compound 39.

HRMS-ESI: m/z calcd for
$C_{30}H_{58}N_2O_{11}$ $[M_8+H]^+$ 622.4035, found 622.4036;
$C_{32}H_{62}N_2O_{12}$ $[M_9+H]^+$ 666.4297, found 666.4296;
$C_{34}H_{66}N_2O_{13}$ $[M_{10}+H]^+$ 710.4559, found 710.4559;
$C_{36}H_{70}N_2O_{14}$ $[M_{10}+H]^+$ 754.4822, found 754.4815.

The entire disclosure of all documents referred to in the present application, such as journal articles, books, patents, and patent applications, is hereby included in this specification by way of reference.

The invention claimed is:

1. A compound of general formula (I)

$$Q_1\text{-}(N)_a\text{-}\underset{R^1}{X}\text{-}M\text{-}Q_2 \quad (I)$$

wherein:
M is $NR^2$ or O;
X is CO or $SO_2$;
a is 1 or 0;
$R^1$ is H; $(CH_2)_o$-E, wherein o is an integer from 1 to 10 and E is COOH, OH, $NH_2$, N3, C≡CH, $P(O)(OH)_2$, $P(O)(OR^{13})_2$, $P(O)(OR^{13})(R^{13})$, $P(O)R^{13}_2$ or $SSO_2Me$; $(CH_2-CH_2-O)_m-CH_3$ or $(CH_2-CH_2-O)_m-H$, wherein m is an integer from 1 to 500; or <chemical structure: (CH2)p-triazole-N-(CH2CH2O)q-> wherein p is an integer from 0 to 7 and q is an integer from 1 to 500;
$R^2$ is, independently, as defined for $R^1$;
or
if X is CO, a is 1 and M is $NR^2$, $R^1$ and $R^2$ form together with the group X and the atoms to which they are bound a 5- or 6-membered heterocyclic ring which may be substituted;
and
$Q_1$ and $Q_2$ are a cyclic nitroxide of formula:

<chemical structure>

2. The compound of claim 1, wherein
M is $NR_2$; and
$R_2$ is hydrogen;
or
if X is CO, a is 1 and M is $NR_2$, $R_1$ and $R_2$ together form a bridging —$CH_2CHG$- or —$CH_2CH_2CHG$- or —$CH_2CH(G)CH_2$— group, with G=$(CH_2)_o$-E, wherein o is an integer from 0 to 10 and E is: COOH, OH, $NH_2$, N3, C≡CH or $SSO_2Me$; or $(CH_2-CH_2-O)_m-CH_3$, wherein m is an integer from 1 to 500; or a bridging —$CH_2CH_2$—, —$CH_2CH_2CH_2$— or —$CH_2-CHOH-CH_2$— group.

3. The compound of claim 1, wherein
a is 1, when X is $SO_2$, and 0 or 1, when X is CO;
M is $NR_2$; and
$R_2$ is hydrogen;
$R_1$ is H; $(CH_2)_o$-E, wherein o is an integer from 1 to 10 and E is COOH or $(CH_2-CH_2-O)_m-CH_3$ or $(CH_2-CH_2-O)_m-H$, wherein m is an integer from 1 to 500;
or <chemical structure: (CH2)p-triazole-N-(CH2CH2O)q-> wherein p is an integer from 0 to 7 and q is an integer from 1 to 500;
or
if X is CO, a is 1 and M is $NR_2$, $R_1$ and $R_2$ together form a bridging —$CH_2CH(G)CH_2$— group, with G=$(CH_2)_o$-E, wherein o is an integer from 0 to 10 and E is: COOH, OH or $NH_2$; or $(CH_2-CH_2-O)_m$, —$CH_3$, wherein m is an integer from 1 to 500; or a bridging —$CH_2CH_2$—, —$CH_2CH_2CH_2$— or —$CH_2-CHOH-CH_2$— group.

4. The compound of claim 1, wherein
X is CO;
a is 1,
$R_1$ is H; or $(CH_2-CH_2-O)_m-CH_3$ or $(CH_2-CH_2-O)_m-H$, wherein m is an integer from 1 to 500; or <chemical structure: (CH2)p-triazole-N-(CH2CH2O)q-> wherein p is an integer from 0 to 7 and q is an integer from 1 to 500;
or
$R_1$ and $R_2$ together form a bridging group —$CH_2CH(G)CH_2$— wherein G is $(CH_2-CH_2-O)_m-CH_3$ with m being an integer from 1 to 500, or a bridging —$CH_2CH_2$—, —$CH_2-CHOH-CH_2$— or —$CH_2CH_2CH_2$— group.

5. The compound of claim 4, wherein m is an integer from 1 to 15.

6. The compound of claim 1, which is selected from

56

<chemical structure: bis-nitroxide urea>

(15-{[(7oxyl-3,11-dioxa-7-azadispiro[5.1.5.3]hexadec-15-yl)carbamoyl]amino}-[3,11-dioxa-7-azadispiro[5.1.5.3]hexadec-7-yl])oxidanyl), designated as "bPyTurea" or "PyPOL";

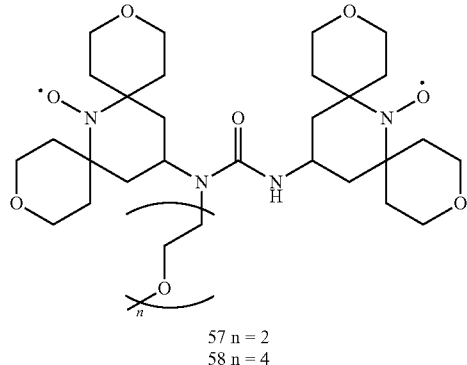

57 n = 2
58 n = 4

57: (15-{[(7-oxyl-3,11-dioxa-7-azadispiro[5.1.5.3]hexadec-15-yl)carbamoyl][2-(2-methoxyethoxy)ethyl]amino}-[3,11-dioxa-7-azadispiro[5.1.5.3]hexadec-7-yl])oxidanyl, designated as "bPyTureaPEG2";

58: (15-{[(7-oxyl-3,11-dioxa-7-azadispiro[5.1.5.3]hexadec-15-yl)carbamoyl][2-(2,5,8,11-tetraoxatridecan-13-ylamino)}-[3,11-dioxa-7-azadispiro[5.1.5.3]hexadec-7-yl)oxidanyl, designated as "bPyTureaPEG4" or "AMUPOL";

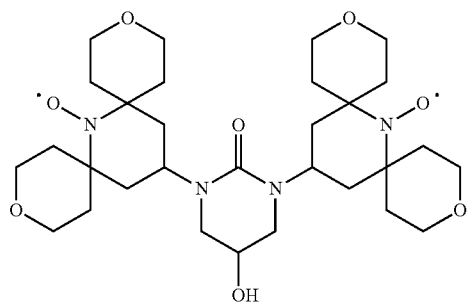

5-hydroxy-1,3-bis(7-oxyl-3,11-dioxa-7-azadispiro[5.1.5.3]hexadec-15-yl)tetrahydropyrimidin-2(1H)-one; designated as "PyPOLC6OH";

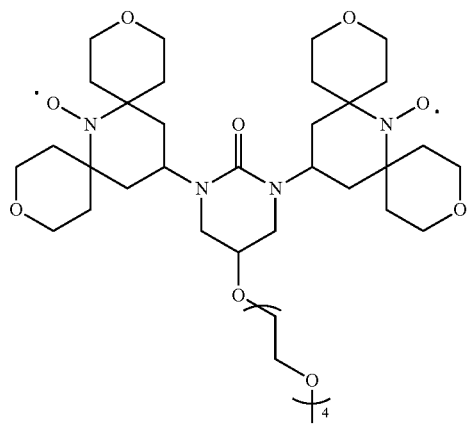

1,3-bis(7-oxyl-3,11-dioxa-7-azadispiro[5.1.5.3]hexadec-15-yl)-5-(2,5,8,11-tetraoxatridecan-13-yloxy)tetrahydropyrimidin-2(1H)-one;

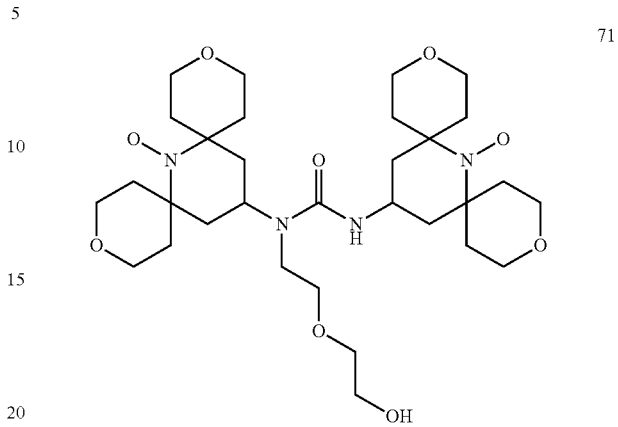

(15-{[(7-oxyl-3,11-dioxa-7-azadispiro[5.1.5.3]hexadec-15-yl)carbamoyl][2-(2-hydroxyethoxy)ethyl]amino}-[3,11-dioxa-7-azadispiro[5.1.5.3]hexadec-7-yl])oxidanyl, designated as "PyPOLPEG2OH";

and

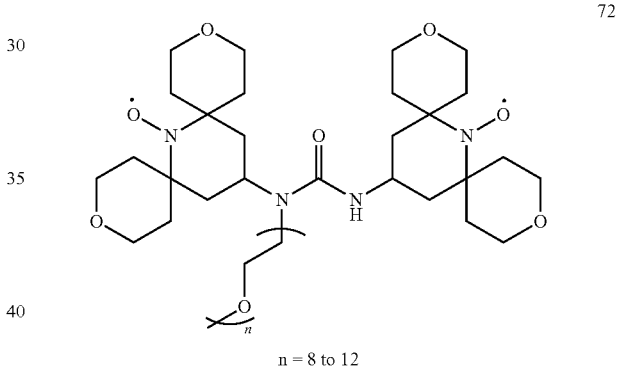

n = 8 to 12

α-{(7-oxyl-3,11-dioxa-7-azadispiro[5.1.5.3]hexadec-15-yl)[(7-oxyl-3,11-dioxa-7-azadispiro[5.1.5.3]hexadec-15-yl)carbamoyl]amino}ω-methylpoly(ethane-1,2-diyloxy), designated as "PyPOLPEG10".

7. A method for polarizing NMR-active nuclear spins of an analyte, comprising:

preparing a sample comprising the analyte and the compound of claim 1 as a Dynamic Nuclear Polarization (DNP) agent; and analyzing the sample by Nuclear Magnetic Resonance (NMR) spectroscopy.

8. The method of claim 7, wherein the NMR spectroscopy is Solid State NMR (SS-NMR) spectroscopy.

9. The method of claim 7, wherein the NMR spectroscopy is liquid state NMR spectroscopy.

10. The method of claim 7, wherein the NMR spectroscopy is Magnetic Resonance Imaging (MRI).

11. The method of claim 7, wherein the analyte is a solid inorganic, organic or metallo-organic material having an crystal lattice or an amorphous solid structure, a molecular chemical or biochemical compound including polymeric and macromolecular compounds, or a biological entity.

12. The method of claim 11, wherein the molecular chemical or biochemical compound is an isolated inorganic, organic, metallo-organic or biochemical compound or an inorganic, organic or biochemical compound in its natural biological environment.

13. The method of claim 7, wherein nuclei having an NMR-active spin are selected from $^{1}$H, $^{2}$H, $^{6}$Li, $^{7}$Li, $^{10}$B, $^{11}$B, $^{13}$C, $^{14}$N, $^{15}$N, $^{17}$O, $^{19}$F, $^{23}$Na, $^{25}$Mg, $^{27}$Al, $^{29}$Si, $^{31}$P, $^{33}$S, $^{35}$Cl, $^{37}$Cl, $^{39}$K, $^{41}$K, $^{43}$Ca, $^{47}$Ti, $^{49}$Ti, $^{50}$V, $^{51}$V, $^{53}$Cr, $^{77}$Se, $^{89}$Y, $^{117}$Sn, $^{119}$Sn, and $^{199}$Hg.

14. The method of claim 7, wherein preparing the sample comprises dissolving the analyte in an aqueous medium, an organic solvent or solvent mixture or an aqueous/organic solvent mixture.

15. The method of claim 7, where the DNP agent is in a solid state, a liquid state or a dissolved liquid state during the polarization time.

16. The method of claim 15, wherein the solid state is a frozen solution comprising a frozen solvent or solvent mixture containing the analyte and the DNP agent.

17. The method of claim 15, wherein the DNP agent in the solid state is chemically bound to analyte or dispersed in the analyte without a solvent present.

18. The method of claim 7, wherein the DNP agent concentration is from about 1 to about 200 mM.

19. The method of claim 7, wherein the temperature of a sample containing the analyte and the DNP agent is from about 1 to about 200 K during the polarization time.

20. The method of claim 7, wherein a frequency of microwave irradiation is in the range from about 5 to about 800 GHz.

21. The method of claim 7, wherein either a static or a spinning sample experimental setup is used.

* * * * *